US012000811B2

(12) United States Patent
Yan et al.

(10) Patent No.: US 12,000,811 B2
(45) Date of Patent: *Jun. 4, 2024

(54) METHOD AND SYSTEM OF IDENTIFYING AND QUANTIFYING ANTIBODY FRAGMENTATION

(71) Applicant: Regeneron Pharmaceuticals, Inc., Tarrytown, NY (US)

(72) Inventors: Yuetian Yan, Chappaqua, NY (US); Shunhai Wang, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/951,614

(22) Filed: Sep. 23, 2022

(65) Prior Publication Data

US 2023/0314388 A1      Oct. 5, 2023

Related U.S. Application Data

(63) Continuation of application No. 16/743,296, filed on Jan. 15, 2020, now Pat. No. 11,486,864.

(60) Provisional application No. 62/793,004, filed on Jan. 16, 2019.

(51) Int. Cl.
*G01N 30/72* (2006.01)
*G01N 33/563* (2006.01)
*G01N 33/68* (2006.01)

(52) U.S. Cl.
CPC ....... *G01N 30/7266* (2013.01); *G01N 33/563* (2013.01); *G01N 33/6857* (2013.01)

(58) Field of Classification Search
CPC ............ G01N 33/6857; G01N 33/563; G01N 30/7266
USPC ........................................................ 73/61.55
See application file for complete search history.

(56) References Cited

U.S. PATENT DOCUMENTS

| 2005/0059013 A1* | 3/2005 | Chan | A61P 35/00 |
| | | | 435/6.12 |
| 2010/0240543 A1* | 9/2010 | Liotta | G01N 33/54346 |
| | | | 435/6.12 |
| 2015/0316515 A1 | 11/2015 | Lauber | |
| 2020/0132697 A1 | 4/2020 | Yan | |

FOREIGN PATENT DOCUMENTS

WO    WO2016018978 A1    2/2016

OTHER PUBLICATIONS

Markus Haberger et al., "Rapid characterization of biotherapeutic proteins by size-exclusion chromatography coupled to native mass spectrometry," MABS, vol. 8, No. 2, Dec. 10, 2015, pp. 331-339.
Yan He et al., "On-line coupling of size exclusion chromatography with mixed-mode liquid chromatography for comprehensive profiling of biopharmaceutical drug product," Journal of Chromatography A, vol. 1262, Sep. 10, 2012, pp. 122-129.

(Continued)

*Primary Examiner* — Kiet T Nguyen
(74) *Attorney, Agent, or Firm* — Kramer Levin Naftalis & Frankel LLP

(57) ABSTRACT

Methods and system for identifying and quantifying antibody fragments and identifying the site of fragmentation on an antibody are provided herein.

21 Claims, 21 Drawing Sheets

(56) References Cited

OTHER PUBLICATIONS

Wong Cintyu et al., "Facile method of quantification for oxidized tryptophan degradants of monoclonal antibody by mixed mode ultra performance liquid chromatography," Journal of Chromatography A, vol. 1270, Nov. 5, 2012, pp. 153-161.
International Search Report PCT Application No. PCT/US2020/013648, International Filing Date Jan. 15, 2020, dated May 27, 2020.
Anthony Ehkirch et al., Hyphenation of size exclusion chromatography to native ion mobility mass spectrometry for the analytical characterization of therapeutic antibodies, Journal of Chromatography B, 2018, 1086, 176-183.

* cited by examiner

METHOD AND SYSTEM OF IDENTIFYING AND QUANTIFYING ANTIBODY FRAGMENTATION

CROSS-REFERENCE TO RELATED APPLICATIONS

This application is a continuation of U.S. patent application Ser. No. 16/743,296, filed Jan. 15, 2020, which claims the benefit of U.S. Provisional Application No. 62/793,004, filed Jan. 16, 2019, which is herein incorporated by reference in its entirety.

FIELD OF THE INVENTION

The invention generally pertains to a method and system for identifying and quantifying antibody fragments and identifying the site of fragmentation on an antibody.

BACKGROUND

Protein based biopharmaceutical products have emerged as important drugs for the treatment of cancer, autoimmune disease, infection and cardiometabolic disorders, and they represent one of the fastest growing product segments of the pharmaceutical industry.

Protein digestion, either enzymatically or non-enzymatically, is an important tool in protein identification, characterization, and quantification. The site of fragmentation can depend on the protein complexity and/or the method of digestion. In order to detect the site of the fragmentation, identification of the clipped fragments is required.

Further, protein based biopharmaceuticals must meet very high standards of purity. Proteins are susceptible to cleavage of the peptide backbone into fragments, which can be catalyzed by acidic conditions used during processing, handling, or storage. These clipped fragments could exhibit a different mode of action and potential toxicity or immunogenicity compared to the product. In addition, they can have a lower stability than the product, which presents a higher risk for aggregation and immunogenicity. Despite recent advances, it remains a challenge to develop purity assay methods for quantitative evaluation of such clipped fragments. Therefore, it is important to monitor and characterize such clipped fragments during different stages of drug development and production.

Analytical method for assays for detection of fragments should display sufficient accuracy and resolution to detect and quantify the desired product. Evaluation can be difficult due to similarities between structural and physicochemical properties of the protein and the clipped fragment(s). Direct analysis can require isolation of the clipped fragment(s) in a sufficiently large amount for the assay, which can be undesirable and has only been possible in selected cases.

There is a long felt need in the art for a method and/or system for identifying and quantifying antibody fragments and identifying the site of fragmentation on an antibody.

SUMMARY

Growth in the development, manufacture and sale of protein-based biopharmaceutical products has led to an increasing demand for characterizing fragments of a protein and site of fragmentation of a protein.

Exemplary embodiments disclosed herein satisfy the aforementioned demands by providing methods and systems for identifying and quantifying antibody fragments and identifying the site of fragmentation on an antibody.

This disclosure, at least in part, provides a method for quantifying a fragment of an antibody in a sample.

In one exemplary embodiment, the method for quantifying a fragment of an antibody can comprise contacting the sample to a chromatographic system having a mixed-mode size-exclusion chromatography resin with an additional functionality, washing the mixed-mode size-exclusion chromatography resin using a mobile phase to provide an eluent including the fragment, and quantifying an amount of the fragment in the eluent using a mass spectrometer.

In one aspect of this embodiment, the method for quantifying a fragment of an antibody in a sample can comprise contacting the sample to a chromatographic system having a mixed-mode size-exclusion chromatography resin with a hydrophobic interaction functionality In one aspect of this embodiment, the method for quantifying a fragment of an antibody in a sample can comprise contacting the sample to a chromatographic system having a mixed-mode size-exclusion chromatography resin with charge-charge interaction functionality.

In one aspect of this embodiment, the method for quantifying a fragment of an antibody in a sample can comprise contacting about 10 µg to about 100 µg of a sample to a chromatographic system having a mixed-mode size-exclusion chromatography resin with an additional functionality.

In one aspect of this embodiment, the method for quantifying a fragment of an antibody in a sample can comprise washing the mixed-mode size-exclusion chromatography resin using a mobile phase to provide an eluent including the fragment. In a specific aspect of this embodiment, the method for quantifying a fragment of an antibody in a sample can comprise washing the mixed-mode size-exclusion chromatography resin using a mobile phase that can be compatible with a mass spectrometer. In another specific aspect, the method for quantifying a fragment of an antibody in a sample can comprise washing the mixed-mode size-exclusion chromatography resin using a mobile phase, wherein the mobile phase can be selected from ammonium acetate, ammonium bicarbonate, or ammonium formate, or combinations thereof.

In one aspect of this embodiment, the method for quantifying a fragment of an antibody in a sample can comprise washing the mixed-mode size-exclusion chromatography resin using a mobile phase containing up to 600 mM total salt concentration.

In one aspect of this embodiment, the method for quantifying a fragment of an antibody in a sample can comprise washing the mixed-mode size-exclusion chromatography resin using a mobile phase with a flow rate of 0.2 ml/min to 0.4 ml/min.

In one aspect of this embodiment, the method for quantifying a fragment of an antibody in a sample can comprise contacting the sample to a chromatographic system having a mixed-mode size-exclusion chromatography resin with an additional functionality, wherein the fragment can be a degradation product of the antibody.

In one aspect of this embodiment, the method for quantifying a fragment of an antibody in a sample can comprise contacting the sample to a chromatographic system having a mixed-mode size-exclusion chromatography resin with an additional functionality, wherein the fragment is an impurity.

In one aspect of this embodiment, the method for quantifying a fragment of an antibody in a sample can comprise contacting the sample to a chromatographic system having a mixed-mode size-exclusion chromatography resin with an additional functionality, wherein the antibody is a monoclonal antibody.

In one aspect of this embodiment, the method for quantifying a fragment of an antibody in a sample can comprise contacting the sample to a chromatographic system having a mixed-mode size-exclusion chromatography resin with an additional functionality, wherein the antibody is a therapeutic antibody.

In one aspect of this embodiment, the method for quantifying a fragment of an antibody in a sample can comprise contacting the sample to a chromatographic system having a mixed-mode size-exclusion chromatography resin with an additional functionality, wherein the antibody is a bispecific antibody.

In one aspect of this embodiment, the method for quantifying a fragment of an antibody in a sample can comprise contacting the sample to a chromatographic system having a mixed-mode size-exclusion chromatography resin with an additional functionality, wherein the antibody is a multispecific antibody.

In one aspect of this embodiment, the method for quantifying a fragment of an antibody in a sample can comprise quantifying an amount of the fragment in said eluent using a mass spectrometer, wherein the mass spectrometer can be a tandem mass spectrometer.

This disclosure, at least in part, provides a method for identifying a fragment of an antibody in a sample.

In one exemplary embodiment, the method for identifying a fragment of an antibody in a sample can comprise contacting the sample to a chromatographic system having a mixed-mode size-exclusion chromatography resin with an additional functionality, washing the mixed-mode size-exclusion chromatography resin using a mobile phase to provide an eluent including the fragment, determining the molecular weight of the fragment in the eluent using a mass spectrometer, and correlating the molecular weight data of the fragment to data obtained from at least one known protein standard.

In one aspect of this embodiment, the method for identifying a fragment of an antibody in a sample can comprise contacting said sample to a chromatographic system having a mixed-mode size-exclusion chromatography resin with a hydrophobic interaction functionality In one aspect of this embodiment, the method for identifying a fragment of an antibody in a sample can comprise contacting said sample to a chromatographic system having a mixed-mode size-exclusion chromatography resin with charge-charge interaction functionality.

In one aspect of this embodiment, the method for identifying a fragment of an antibody in a sample can comprise contacting about 10 μg to about 100 μg of a sample to a chromatographic system having a mixed-mode size-exclusion chromatography resin with an additional functionality.

In one aspect of this embodiment, method for identifying a fragment of an antibody in a sample can comprise washing the mixed-mode size-exclusion chromatography resin using a mobile phase to provide an eluent including the fragment.

In one aspect of this embodiment, the method for identifying a fragment of an antibody in a sample can comprise washing the mixed-mode size-exclusion chromatography resin using a mobile phase that can be compatible with a mass spectrometer. In a specific aspect, the method for identifying a fragment of an antibody in a sample can comprise washing the mixed-mode size-exclusion chromatography resin using a mobile phase, wherein the mobile phase can be selected from ammonium acetate, ammonium bicarbonate, or ammonium formate, or combinations thereof. In another specific aspect, the method for method for identifying a fragment of an antibody in a sample can comprise washing the mixed-mode size-exclusion chromatography resin using a mobile phase containing up to 600 mM total salt concentration.

In one aspect of this embodiment, the method for identifying a fragment of an antibody in a sample can comprise washing the mixed-mode size-exclusion chromatography resin using a mobile phase with a flow rate of 0.2 ml/min to 0.4 ml/min.

In one aspect of this embodiment, the method for identifying a fragment of an antibody in a sample can comprise contacting the sample to a chromatographic system having a mixed-mode size-exclusion chromatography resin with an additional functionality, wherein the fragment is a degradation product of the antibody.

In one aspect of this embodiment, the method for identifying a fragment of an antibody in a sample can comprise contacting the sample to a chromatographic system having a mixed-mode size-exclusion chromatography resin with an additional functionality, wherein the antibody is a monoclonal antibody.

In one aspect of this embodiment, the method for identifying a fragment of an antibody in a sample can comprise contacting the sample to a chromatographic system having a mixed-mode size-exclusion chromatography resin with an additional functionality, wherein the antibody is a therapeutic antibody.

In one aspect of this embodiment, the method for identifying a fragment of an antibody in a sample can comprise contacting the sample to a chromatographic system having a mixed-mode size-exclusion chromatography resin with an additional functionality, wherein the antibody is a bispecific antibody.

In one aspect of this embodiment, the method for identifying a fragment of an antibody in a sample can comprise contacting the sample to a chromatographic system having a mixed-mode size-exclusion chromatography resin with an additional functionality, wherein the antibody is a multispecific antibody.

In one aspect of this embodiment, the method for identifying a fragment of an antibody in a sample can comprise contacting the sample to a chromatographic system having a mixed-mode size-exclusion chromatography resin with an additional functionality, wherein the fragment can be a digestion product of the antibody.

In one aspect of this embodiment, the method for identifying a fragment of an antibody in a sample can comprise quantifying an amount of the fragment in said eluent using a mass spectrometer, wherein the mass spectrometer can be a tandem mass spectrometer.

The disclosure, at least in part, provides a method for identification of a site of fragmentation of an antibody.

In one exemplary embodiment, the method for identification of a site of fragmentation of an antibody can comprise contacting a sample including fragments of an antibody to a chromatographic system having a mixed-mode size-exclusion chromatography resin with an additional functionality, washing the mixed-mode size-exclusion chromatography resin using a mobile phase to provide an eluent, determining molecular weight data of the fragments of the antibody in said eluent using a mass spectrometer, and correlating the molecular weight data of the fragments to data obtained from at least one known protein standard.

In one aspect of this embodiment, the method for identification of a site of fragmentation of an antibody can comprise contacting a sample including fragments of an antibody to a chromatographic system having a mixed-mode size-exclusion chromatography resin with a hydrophobic interaction functionality In one aspect of this embodiment, the method for identification of a site of fragmentation of an antibody can comprise contacting a sample including fragments of an antibody to a chromatographic system having a mixed-mode size-exclusion chromatography resin with charge-charge interaction functionality.

In one aspect of this embodiment, the method for identification of a site of fragmentation of an antibody can comprise contacting about 10 µg to about 100 µg of a sample including fragments of an antibody to a chromatographic system having a mixed-mode size-exclusion chromatography resin with an additional functionality.

In one aspect of this embodiment, the method for identification of a site of fragmentation of an antibody can comprise contacting a sample including fragments of an antibody to a chromatographic system having a mixed-mode size-exclusion chromatography resin with charge-charge interaction functionality and washing the mixed-mode size-exclusion chromatography resin using a mobile phase to provide an eluent including the fragments.

In one aspect of this embodiment, the method for identification of a site of fragmentation of an antibody can comprise washing the mixed-mode size-exclusion chromatography resin using a mobile phase that can be compatible with a mass spectrometer. In a specific aspect, the method for identification of a site of fragmentation of an antibody can comprise washing the mixed-mode size-exclusion chromatography resin using a mobile phase, wherein the mobile phase can be selected from ammonium acetate, ammonium bicarbonate, or ammonium formate, or combinations thereof. In another specific aspect, the method for identification of a site of fragmentation of an antibody can comprise washing the mixed-mode size-exclusion chromatography resin using a mobile phase containing up to 600 mM total salt concentration.

In one aspect of this embodiment, the method for identification of a site of fragmentation of an antibody can comprise washing the mixed-mode size-exclusion chromatography resin using a mobile phase with a flow rate of 0.2 ml/min to 0.4 ml/min.

In one aspect of this embodiment, the method for identification of a site of fragmentation of an antibody can comprise contacting a sample including fragments of an antibody to a chromatographic system having a mixed-mode size-exclusion chromatography resin with an additional functionality, wherein the antibody can be a monoclonal antibody.

In one aspect of this embodiment, the method for identification of a site of fragmentation of an antibody can comprise contacting a sample including fragments of an antibody to a chromatographic system having a mixed-mode size-exclusion chromatography resin with an additional functionality, wherein the antibody can be a therapeutic antibody.

In one aspect of this embodiment, the method for identification of a site of fragmentation of an antibody can comprise contacting a sample including fragments of an antibody to a chromatographic system having a mixed-mode size-exclusion chromatography resin with an additional functionality, wherein the antibody can be a bispecific antibody.

In one aspect of this embodiment, the method for identification of a site of fragmentation of an antibody can comprise contacting a sample including fragments of an antibody to a chromatographic system having a mixed-mode size-exclusion chromatography resin with an additional functionality, wherein the antibody can be a multispecific antibody.

In one aspect of this embodiment, the method for identification of a site of fragmentation of an antibody can comprise contacting a sample including fragments of an antibody to a chromatographic system having a mixed-mode size-exclusion chromatography resin with an additional functionality, wherein the sample contains more than two fragments.

In one aspect of this embodiment, the method for identification of a site of fragmentation of an antibody can comprise contacting a sample including fragments of an antibody to a chromatographic system having a mixed-mode size-exclusion chromatography resin with an additional functionality, wherein the fragments are formed due to degradation of the antibody.

In one aspect of this embodiment, the method for identification of a site of fragmentation of an antibody can comprise contacting a sample including fragments of an antibody to a chromatographic system having a mixed-mode size-exclusion chromatography resin with an additional functionality, wherein the fragments are digestion products of the antibody.

In one aspect of this embodiment, the method for identification of a site of fragmentation of an antibody can comprise contacting a sample including fragments of an antibody to a chromatographic system having a mixed-mode size-exclusion chromatography resin with an additional functionality, wherein the fragments are formed due to degradation of the antibody.

In one aspect of this embodiment, the method for identification of a site of fragmentation of an antibody can comprise identifying the fragment in said eluent using a mass spectrometer, wherein the mass spectrometer can be a tandem mass spectrometer.

This disclosure, at least in part, provides a mixed mode chromatographic system.

In one exemplary embodiment, the chromatographic system can comprise a chromatographic column having a mixed-mode size-exclusion chromatography resin with an additional functionality and a mass spectrometer.

In one aspect of this embodiment, the mixed mode chromatographic system can comprise a mixed-mode size-exclusion chromatography resin with hydrophobic interaction functionality.

In one aspect of this embodiment, the mixed mode chromatographic system can comprise a mixed-mode size-exclusion chromatography resin with charge-charge interaction functionality.

In one aspect of this embodiment, the mixed mode chromatographic system can comprise a mixed-mode size-exclusion chromatography resin with an additional functionality, which can be used for elution of about 10 µg to about 100 µg of a sample.

In one aspect of this embodiment, the mixed mode chromatographic system can comprise a mixed-mode size-exclusion chromatography resin capable of receiving a mobile phase.

In one aspect of this embodiment, the mixed mode chromatographic system can comprise a mixed-mode size-exclusion chromatography resin further capable of receiving a sample having a fragment.

In one aspect of this embodiment, the mixed mode chromatographic system can comprise a mixed-mode size-exclusion chromatography resin capable of being washed with a mobile phase.

In one aspect of this embodiment, the mixed mode chromatographic system can comprise a mass spectrometer coupled to a chromatographic column having a mixed-mode size-exclusion chromatography resin with an additional functionality.

In one aspect of this embodiment, the mixed mode chromatographic system can comprise a tandem mass spectrometer.

In one aspect of this embodiment, the mixed mode chromatographic system can comprise a chromatographic column having a having a mixed-mode size-exclusion chromatography resin with an additional functionality, wherein the mixed-mode size-exclusion chromatography resin can be compatible with a mobile phase selected from ammonium acetate, ammonium bicarbonate, or ammonium formate, or combinations thereof.

In one aspect of this embodiment, the mixed mode chromatographic system can comprise a chromatographic column having a having a mixed-mode size-exclusion chromatography resin with an additional functionality, wherein the mixed-mode size-exclusion chromatography resin can be washed using a mobile phase containing up to 600 mM total salt concentration.

In one aspect of this embodiment, the mixed mode chromatographic system can comprise a chromatographic column having a having a mixed-mode size-exclusion chromatography resin with an additional functionality, wherein the chromatographic column can be washed with a mobile phase with a flow rate of 0.2 ml/min to 0.4 ml/min.

DETAILED DESCRIPTION

Antibody fragmentation, either enzymatically or non-enzymatically, can form antibody fragments as impurities during the processing of the antibody products. The enormous dynamic proteinaceous species present in protein-based therapeutics pose a challenge for current mass spectrometry-based methods to detect antibody fragments and the site of fragmentation since the amount of the antibody fragments may be in low abundance.

Alternatively, a wide variety of antibody fragments have been designed as therapeutics. The most significant advantages to antibody fragments include size, manufacturing, tissue penetration, and ability to concatenate to generate multi-specificity. Sometimes it is useful to study or make use of the activity of one portion of an immunoglobulin without interference from other portions of the molecule. It is possible to selectively cleave the immunoglobulin molecule into fragments that have discrete characteristics. Antibody fragmentation can be accomplished using reducing agents and proteases that digest or cleave certain portions of the immunoglobulin protein structure (Nelson (2010) mAbs 2:77-83; 12—Antibody fragments as therapeutics, Editor(s): William R. Strohl, Lila M. Strohl, In Woodhead Publishing Series in Biomedicine, "Therapeutic Antibody Engineering, 2012, 265-595). In order to design and evaluate such antibody fragments, it can be important to identify the antibody fragments and the site of fragmentation on the antibody by a particular digestive method.

To identify the antibody fragments and the site of fragmentation, traditional separation-based antibody purity assays such as electrophoresis- and high-performance liquid chromatography (HPLC)-based methods lack the needed resolution. Peptide mapping via reverse phase liquid chromatography (RPLC) coupled with mass spectrometry also has some limitations as the sample preparation process for RP-LC-MS is lengthy, and in some cases the chromatographic conditions such as high temperature, organic solvents, and acidic pH could induce oxidation artifacts. Hydrophobic interaction chromatography (HIC) and Protein A chromatography also has been used for analysis of antibody oxidation, but can require longer chromatographic run times, and can have a limited power for different fragments (Haverick et al. mAbs, (2014) 6:852-858; Boyd et al. J. Chromatogr. B Analyt. Technol. Biomed. Life Sci. (2011) 879: 955-960; and Loew et al. J. Pharm. Sci. (2012) 101: 4248-4257).

Figure 1:
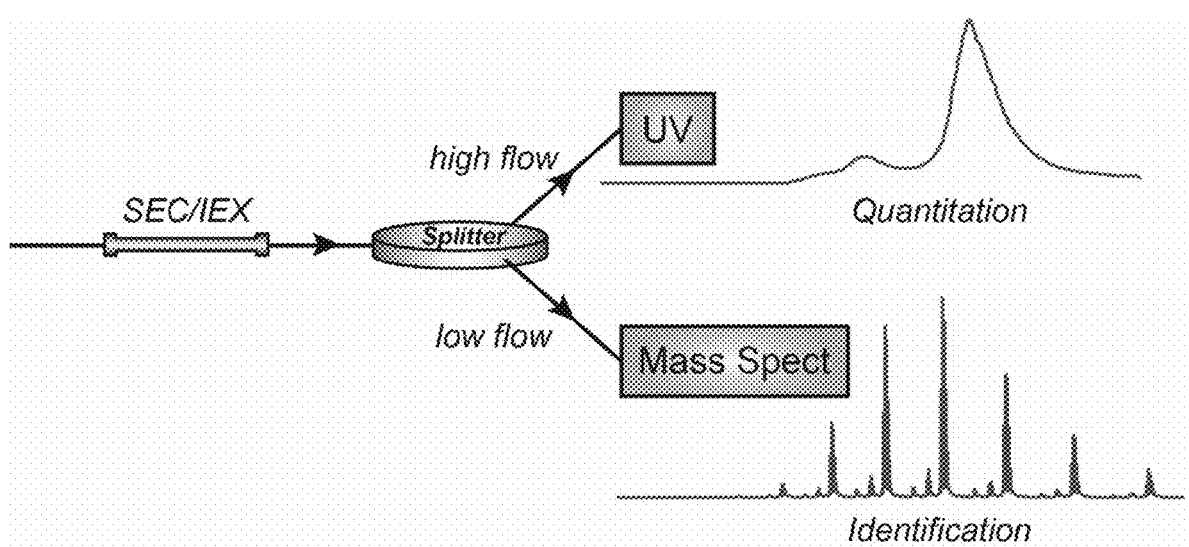
FIG. 1 shows represents an example of a system used for quantifying and/or identifying protein variants using size exclusion chromatography or ion exchange chromatography.

Additionally, some size exclusion chromatography or ion exchange chromatography methods can be used for separating antibody fragments formed on digestion of an antibody. The antibody fragments can further be analyzed using a mass spectrometer or ultraviolet absorbance system. However, the mobile phase from the size exclusion chromatography or ion exchange chromatography column cannot be directly injected into the mass spectrometer and requires additional steps including a change in the mobile phase (See FIG. 1).

Considering the limitations of existing methods, an effective and efficient method for identification and quantification of antibody fragments and site of antibody fragmentation using a novel mixed mode—size exclusion chromatography—mass spectrometry system was developed.

Unless defined otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

Biopharmaceutical products are required to show high levels of potency, purity, and low level of structural heterogeneity. Structural heterogeneity often affects the bioactivity and efficacy of a drug. Therefore, characterizing and quantifying the therapeutic protein and/or the impurities is important in pharmaceutical drug development. Structural heterogeneity in a protein can arise from post-translational modifications as well as inherent chemical modifications during manufacturing and storage conditions. For proteins produced in the biotechnology industry, complementary separation techniques are necessary both to purify the target protein and to give an accurate picture of the quality of the final product. The complexity of the product eliminates the use of simple one-dimensional separation strategies.

As used herein, the term "protein" includes any amino acid polymer having covalently linked amide bonds. Proteins comprise one or more amino acid polymer chains, generally known in the art as "polypeptides". "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides' refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a review discussing biotherapeutic proteins and their production, see Ghaderi et al., "Production platforms for biotherapeutic glycoproteins. Occurrence, impact, and challenges of non-human sialylation," (Biotechnol. Genet. Eng. Rev. (2012) 147-75). In some exemplary embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

In some exemplary embodiments, the protein can be an antibody, a bispecific antibody, a multispecific antibody, antibody fragment, monoclonal antibody, or combinations thereof.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_{H2}$ and $C_H3$. Each light chain comprises a light chain variable region (abbreviated herein as LCVR or $V_L$) and a light chain constant region. The light chain constant region comprises one domain (C.sub.L1). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different exemplary embodiments, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

As used herein, the term "digestion" refers to hydrolysis of the peptide bonds of the proteins. There are several approaches to carrying out digestion of a protein in a sample using an appropriate hydrolyzing agent, for example, enzymatic digestion or non-enzymatic digestion.

As used herein, the term "hydrolyzing agent" refers to any one or combination of a large number of different agents that can perform digestion of a protein. Non-limiting examples of hydrolyzing agents that can carry out enzymatic digestion include trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus Saitoi*. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion see Switazar et al., "Protein Digestion: An Overview of the Available Techniques and Recent Developments" (J. Proteome Research 2013, 12, 1067-1077). One or a combination of hydrolyzing agents can cleave peptide bonds in a protein or polypeptide, in a sequence-specific manner, generating a predictable collection of shorter peptides.

One of the widely accepted methods for digestion of proteins in a sample involved the use of proteases. Many proteases are available and each of them has their own characteristics in terms of specificity, efficiency, and optimum digestion conditions. Proteases refer to both endopeptidases and exopeptidases, as classified on the basis of the ability of the protease to cleave at non-terminal or terminal amino acids within the peptide. Alternatively, proteases also refer to the six distinct classes, aspartic, glutamic, and metalloproteases, cysteine, serine, and threonine proteases, as classified on the mechanism of catalysis. The terms "protease" and "peptidase" are used interchangeably to refer to enzymes which hydrolyze peptide bonds.

Proteases can also be classified into specific and non-specific proteases. As used herein, the term "specific protease" refers to a protease with an ability to cleave the peptide substrate at a specific amino acid side chain of a peptide.

As used herein, the term "non-specific protease" refers to a protease with a reduced ability to cleave the peptide substrate at a specific amino acid side chain of a peptide. A cleavage preference may be based on the ratio of the number of a particular amino acid as the site of cleavage to the total number of cleaved amino acids in the protein sequences.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

As used herein, the term "chromatography" refers to a process in which a chemical mixture carried by a liquid or gas can be separated into components as a result of differential distribution of the chemical entities as they flow around or over a stationary liquid or solid phase.

As used herein, the term "Mixed Mode Chromatography (MMC)" or "multimodal chromatography" includes a chromatographic method in which solutes interact with stationary phase through more than one interaction mode or mechanism. MMC can be used as an alternative or complementary tool to traditional reversed-phased (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Mixed mode chromatography media can provide unique selectivity that cannot be reproduced by single mode chromatography. Mixed mode chromatography can provide potential cost savings, longer column lifetimes and operation flexibility compared to affinity based methods.

The phrase "size-exclusion chromatography" or "SEC" or "gel filtration" includes a liquid column chromatographic technique that can sort molecules according to their size in solution.

As used herein, the terms "SEC chromatography resin" or "SEC chromatography media" are used interchangeably herein and can include any kind of solid phase used in SEC which separates the impurity from the desired product (e.g., a homodimer contaminant for a bispecific antibody product). The volume of the resin, the length and diameter of the column to be used, as well as the dynamic capacity and flow-rate can depend on several parameters such as the volume of fluid to be treated, concentration of protein in the fluid to be subjected to the process.

As used herein, the term "mixed mode-size exclusion chromatography" or "MM-SEC" can include any chromatographic method which separates proteins through an additional interaction other than the separation based on their size. The additional or secondary interaction can exploit one or more of the following mechanisms: anion exchange, cation exchange, hydrophobic interaction, hydrophilic interaction, charge-charge interaction, hydrogen bonding, pi-pi bonding, and metal affinity. The mixed mode-size exclusion chromatography resin can refer to any kind of solid phase used for MM-SEC separation. Non-limiting examples are Sepax Zenix SEC-300, Waters BEH 300, or Agilent Bio SEC-3.

Figure 2:
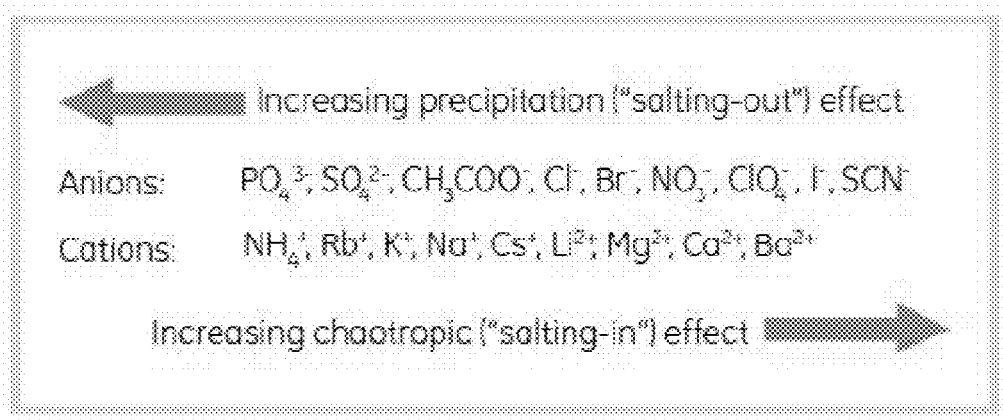
FIG. 2 shows the Hofmeister series showing the effect of anions and cations on protein precipitation (or promoting hydrophobic interaction).

As used herein, the term "hydrophobic functionality" refers to the hydrophobic interaction of the protein with the SEC chromatographic resin as a secondary interaction. They also significantly impact peak shape, which will have a pronounced effect on the resolving ability of the process. Hydrophobic interactions are strongest at high ionic strength of the mobile phase. For selecting a mobile phase to include hydrophobic functionality in a resin, various ions can be arranged in a so-called soluphobic series depending on whether they promote hydrophobic interactions (salting-out effects) or disrupt the structure of water (chaotropic effect) and lead to the weakening of the hydrophobic interaction (See FIG. 2). Cations can be ranked in terms of increasing salting out effect as $Ba^{++}$; $Ca^{++}$; $Mg^{++}$; $Li^+$; $Cs^+$; $Na^+$; $K^+$; $Rb^+$; $NH4^+$, while anions may be ranked in terms of increasing chaotropic effect as $PO^-$; $SO_4^-$; $CH_3CO_2^-$; $Cl^-$; $Br^-$; $NO_3^-$; $ClO_4^-$; $I^-$; $SCN^-$. In general, Na, K or $NH_4$ sulfates effectively promote ligand-protein interaction in HIC. Salts may be formulated that influence the strength of the interaction as given by the following relationship: $(NH_4)_2SO_4$>$Na_2SO_4$>NaCl>$NH_4$Cl>NaBr>NaSCN.

As used herein, the term "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

As used herein, the term "mass analyzer" includes a device that can separate species, that is, atoms, molecules, or clusters, according to their mass. Non-liming examples of mass analyzers that could be employed for fast protein sequencing are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

As used herein, the term "tandem mass spectrometry" includes a technique where structural information on sample molecules is obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or $MS^n$, can be performed by first selecting and isolating a precursor ion ($MS^2$), fragmenting it, isolating a primary fragment ion ($MS^3$), fragmenting it, isolating a secondary fragment ($MS^4$), and so on as long as one can obtain meaningful information or the fragment ion signal is detectable. Tandem MS have been successfully performed with a wide variety of analyzer combinations. What analyzers to combine for a certain application is determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers.

Embodiments disclosed herein provide compositions, methods, and systems for the rapid characterization of proteins in a sample.

As used herein, the terms "include," "includes," and "including," are meant to be non-limiting and are understood to mean "comprise," "comprises," and "comprising," respectively.

This disclosure provides methods for quantifying a fragment of an antibody in a sample comprising contacting the sample to a chromatographic system having a mixed-mode chromatography resin, washing the mixed-mode size-exclusion chromatography resin using a mobile phase to provide an eluent including the fragment, and quantifying the fragment in the eluent using a mass spectrometer.

The disclosure provides methods for identifying a fragment of an antibody in a sample comprising contacting the sample to a chromatographic system having a mixed-mode chromatography resin; washing the mixed-mode chromatography resin using a mobile phase to provide an eluent including the fragment, determining molecular weight of the fragment in the eluent using a mass spectrometer, and correlating the molecular weight data of the fragment to data obtained from at least one known protein standard to identify the fragment.

The disclosure also provides methods for identification of a site of fragmentation of an antibody comprising contacting a sample including fragments of an antibody to a chromatographic system having a mixed-mode size-exclusion chromatography resin with an additional functionality, washing the mixed-mode size-exclusion chromatography resin using a mobile phase to provide an eluent, determining molecular weight data of the fragments of the antibody in said eluent using a mass spectrometer, and correlating the molecular weight data of the fragments to data obtained from at least one known protein standard.

In some specific exemplary embodiments, the chromatographic system can comprise a size-exclusion chromatography resin with an additional interaction.

In some specific exemplary embodiments, the chromatographic system can comprise a size-exclusion chromatography resin with hydrophobic interaction functionality.

In some specific exemplary embodiments, the chromatographic system can comprise a size-exclusion chromatography resin with charge-charge interaction functionality.

In some exemplary embodiments, the fragment can be a digestion product of the antibody. The digestion product can be formed by a hydrolyzing agent. The hydrolyzing agent can include agents carrying out digestion using enzymatic or non-enzymatic digestion. The hydrolyzing agent can be an agent that can carry out digestion using enzymatic digestion and can include trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus saitoi*. The hydrolyzing agent can also be an agent that can carry out digestion using non-enzymatic digestion and can include the use of high temperature, microwave, ultrasound, high pressure, infrared, solvents. The digestion product can be a product-related impurity.

In some exemplary embodiments, the fragment can include Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, triabodies, tetrabodies, linear antibodies, single-chain antibody molecules, and multi specific antibodies formed from antibody fragments.

In some exemplary embodiments, the antibody can be a protein with a pI in the range of about 4.5 to about 9.0. In one aspect, the antibody can be a protein with a pI of about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In some exemplary embodiments, the fragment can be a protein with a pI in the range of about 4.5 to about 9.0. In one aspect, the fragment can be a protein with a pI of about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In one exemplary embodiment, the number of fragments in the sample can be at least two.

In some exemplary embodiments, amount of total protein in the sample loaded on the chromatographic system can range from about 10 μg to about 100 μg. In one exemplary embodiment, the amount of the sample loaded on the chromatographic system can be about 10 μg, about 12.5 μg, about 15 μg, about 20 μg, about 25 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, or about 100 μg.

In some exemplary embodiments, the mobile phase used to elute the fragment can be a mobile phase that can be compatible with a mass spectrometer. In one aspect, the mobile phase can be ammonium acetate, ammonium bicarbonate, or ammonium formate, or combinations thereof.

In one exemplary embodiment, the total concentration of the mobile phase can range up to about 600 mM. In one aspect, the total concentration of the mobile phase can be about 5 mM, about 6 mM, 7 mM, about 8 mM, 9 mM, about 10 mM, 12.5 mM, about 15 mM, 17.5 mM, about 20 mM, 25 mM, about 30 mM, 35 mM, about 40 mM, 45 mM, about 50 mM, 55 mM, about 60 mM, 65 mM, about 70 mM, 75 mM, about 80 mM, 75 mM, about 95 mM, 100 mM, about 110 mM, 120 mM, about 130 mM, 140 mM, about 150 mM, 160 mM, about 170 mM, 180 mM, about 190 mM, 200 mM, about 225 mM, 250 mM, about 275 mM, 300 mM, about 325 mM, 350 mM, about 375 mM, 400 mM, about 4205 mM, 450 mM, about 475 mM, 500 mM, about 525 mM, 550 mM, about 575 mM, or about 600 mM.

In some exemplary embodiments, the mobile phase can have a flow rate of about 0.1 ml/min to about 0.4 ml/min. In one aspect, the flow rate of the mobile phase can be about 0.1 ml/min, about 0.15 ml/min, about 0.20 ml/min, about 0.25 ml/min, about 0.30 ml/min, about 0.35 ml/min, or about 0.4 ml/min.

In one exemplary embodiment, the mass spectrometer can be a tandem mass spectrometer.

In another exemplary embodiment, the mass spectrometer can comprise a nanospray.

In some exemplary embodiments, the antibody can be a monoclonal antibody.

In some exemplary embodiments, the antibody can be a therapeutic antibody.

In some exemplary embodiments, the antibody can be an immunoglobulin protein.

In some exemplary embodiments, the antibody can be a bispecific antibody.

In one exemplary embodiment, the bispecific antibody can be Anti-CD20/CD3 monoclonal antibody.

In one exemplary embodiment, the antibody generated using mouse fibroblast cell line MG87.

In some exemplary embodiments, the fragment can be an antibody fragment formed on digestion of the antibody.

In one exemplary embodiment, the fragment can be a post-translationally modified protein.

In yet another exemplary embodiment, the fragment can be an impurity found in a biopharmaceutical product.

In another exemplary embodiment, the fragment can be an impurity found during the manufacture of the biopharmaceutical product.

In some exemplary embodiments, washing the mixed-mode chromatography resin using a mobile phase requires less than about 30 minutes. In one aspect, the time required for washing the mixed-mode chromatography resin using a mobile phase can be about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 26 minutes, about 27 minutes, about 28 minutes, about 29 minutes, or about 30 minutes.

In some exemplary embodiments, the chromatographic system can be used for at least about 3 sample runs without cleaning. In one aspect, the chromatographic system can be used for at least about 3 sample runs, at least about 4 sample runs, at least about 5 sample runs, at least about 6 sample runs, at least about 7 sample runs, or at least about 8 sample runs, without cleaning.

It is understood that the methods are not limited to any of the aforesaid protein, fragment, impurity, and column and that the methods for identifying or quantifying may be conducted by any suitable means.

Figure 3:
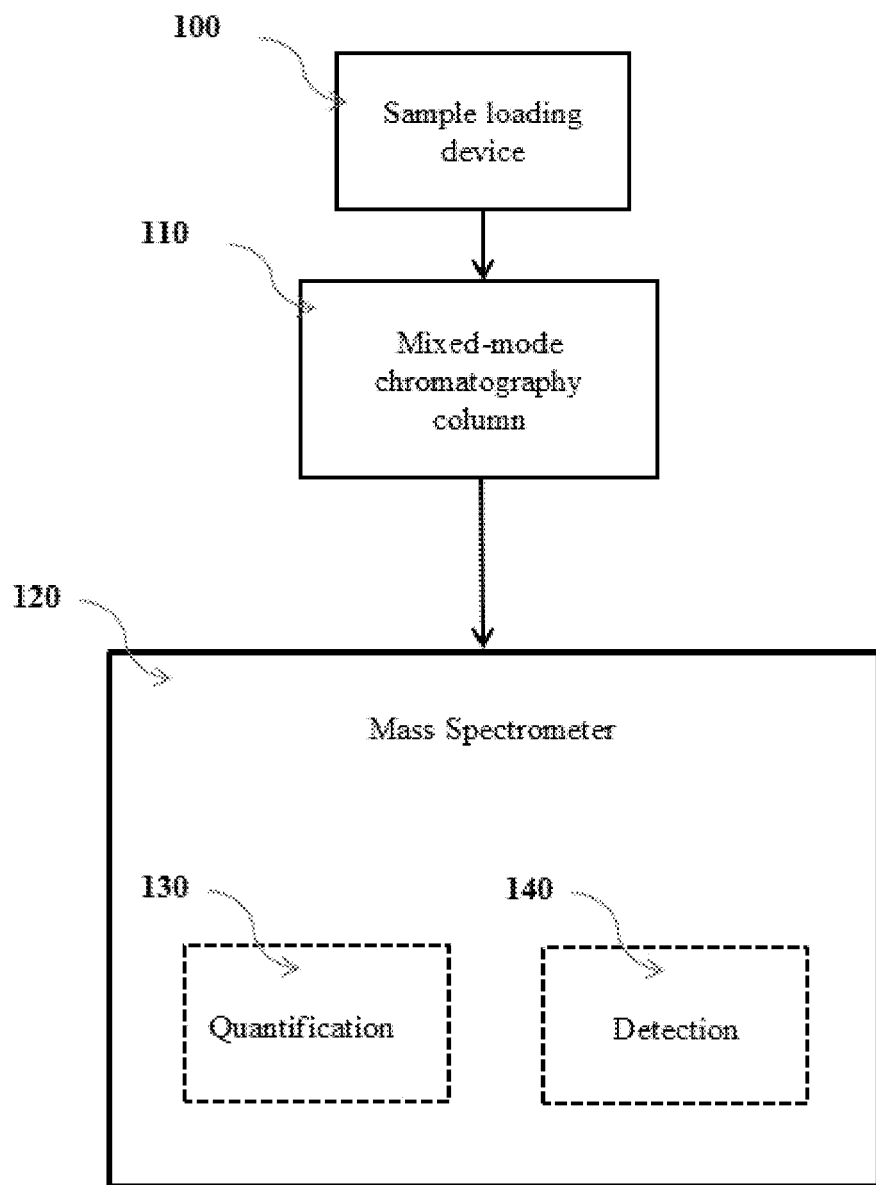
FIG. 3 shows a mixed-mode size exclusion chromatography mass spectrometry system according to an exemplary embodiment.

The disclosure also provides a mixed mode chromatographic system comprising a chromatographic column 110 capable of being washed using a mobile phase to provide an eluent and a mass spectrometer 120 coupled to the chromatographic column 110 (See FIG. 3).

In one exemplary embodiment, the chromatographic column 110 can be capable of being contacted with a sample including a fragment of an antibody using a sample loading device 100.

In some exemplary embodiments, the amount of the sample that can be loaded on the chromatographic column 110 can range from about 10 μg to about 100 μg. In one aspect, the amount of the sample that can be loaded on the chromatographic column 110 can be about 10 μg, about 12.5 μg, about 15 μg, about 20 μg, about 25 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, or about 100 μg.

In some exemplary embodiments, the chromatographic column 110 can be capable of being washed with a mobile phase. In one aspect, the mobile phase can be ammonium acetate, ammonium bicarbonate, or ammonium formate, or combinations thereof.

In one exemplary embodiment, the total concentration of the mobile phase that can be used with the chromatographic column 110 can range up to about 600 mM. In one aspect, the total concentration of the mobile phase that can be used with the chromatographic column 110 can be about 5 mM, about 6 mM, 7 mM, about 8 mM, 9 mM, about 10 mM, 12.5 mM, about 15 mM, 17.5 mM, about 20 mM, 25 mM, about 30 mM, 35 mM, about 40 mM, 45 mM, about 50 mM, 55 mM, about 60 mM, 65 mM, about 70 mM, 75 mM, about 80 mM, 75 mM, about 95 mM, 100 mM, about 100 mM, 120 mM, about 130 mM, 140 mM, about 150 mM, 160 mM, about 170 mM, 180 mM, about 190 mM, 200 mM, about 225 mM, 250 mM, about 275 mM, 300 mM, about 325 mM, 350 mM, about 375 mM, 400 mM, about 425 mM, 450 mM, about 475 mM, 500 mM, about 525 mM, 550 mM, about 575 mM, or about 600 mM.

In another exemplary embodiment, the mobile phase that can be used with the chromatographic column 110 can have a flow rate of 0.1 ml/min to 0.4 ml/min. In one aspect, the flow rate of the mobile phase that can be used with the chromatographic column 110 can be about 0.1 ml/min, about 0.15 ml/min, about 0.20 ml/min, about 0.25 ml/min, about 0.30 ml/min, about 0.35 ml/min, or about 0.4 ml/min.

In one exemplary embodiment, the mobile phase used with the chromatographic column 110 capable of being contacted with a sample including a fragment of an antibody, can be used to elute the fragment.

In some exemplary embodiments, the chromatographic column 110 can be capable of being coupled with a mass spectrometer 120.

In one exemplary embodiment, the mass spectrometer 120 can comprise a nanospray.

In some exemplary embodiments, the mass spectrometer 120 can be a tandem mass spectrometer.

In some exemplary embodiments, the mixed mode chromatographic system can be capable of identifying 140 and/or quantifying 130 a fragment (as illustrated in FIG. 3). The fragment can include Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, triabodies, tetrabodies, linear antibodies, single-chain antibody molecules, and multi specific antibodies formed from antibody fragments.

In one exemplary embodiment, the mixed mode chromatographic system can be used to identify 140 and/or quantify 130 more than one fragments.

In some exemplary embodiments, the mixed mode chromatographic system can be capable of identifying 140 and/or quantifying 130 a fragment of a monoclonal antibody.

In some exemplary embodiments, the mixed mode chromatographic system can be capable of identifying 140 and/or quantifying 130 a fragment of a therapeutic antibody.

In some exemplary embodiments, the mixed mode chromatographic system can be capable of identifying 140 and/or quantifying 130 a fragment of an immunoglobulin protein.

In one exemplary embodiment, the mixed mode chromatographic system can be capable of identifying 140 and/or quantifying 130 a fragment of an IgG1 protein.

In one exemplary embodiment, the mixed mode chromatographic system can be capable of identifying 140 and/or quantifying 130 a fragment of an IgG4 protein.

In one exemplary embodiment, the mixed mode chromatographic system can be capable of identifying 140 and/or quantifying 130 a fragment of a bispecific antibody.

In one exemplary embodiment, the mixed mode chromatographic system can be capable of identifying 140 and/or quantifying 130 a fragment of an Anti-CD20/CD3 monoclonal antibody.

In some exemplary embodiments, the mixed mode chromatographic system can be capable of identifying 140 and/or quantifying 130 a fragment of an antibody fragment formed on digestion of the antibody.

In yet another exemplary embodiment, the mixed mode chromatographic system can be capable of identifying 140 and/or quantifying 130 a fragment which can be an impurity found in a biopharmaceutical product.

In another exemplary embodiment, the mixed mode chromatographic system can be capable of identifying 140 and/or quantifying 130 a fragment, wherein the fragment can be an impurity found during the manufacture of the biopharmaceutical product.

In some exemplary embodiments, the mixed mode chromatographic system can be capable of identifying 140 and/or quantifying 130 a fragment, wherein the fragment can be a protein with a pI in the range of about 4.5 to about 9.0.

In some exemplary embodiments, the mixed mode chromatographic system can be capable of identifying 140 and/or quantifying 130 a fragment, wherein the fragment can be a product-related impurity.

In one exemplary embodiment, the number of fragments in the sample can be at least two.

In some exemplary embodiments, the chromatographic column 110 capable of being used for at least about 3 sample runs without cleaning.

In one exemplary embodiment, the chromatographic column 110 can be used for at least about 3 sample runs, at least about 4 sample runs, at least about 5 sample runs, at least about 6 sample runs, at least about 7 sample runs, or at least about 8 sample runs, without cleaning.

It is understood that the system is not limited to any of the aforesaid protein, impurity, mobile phase, or chromatographic column.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is incorporated by reference, in its entirety and for all purposes, herein.

The disclosure will be more fully understood by reference to the following Examples, which are provided to describe the disclosure in greater detail. They are intended to illustrate and should not be construed as limiting the scope of the disclosure.

EXAMPLES

Example 1. Mixed Mode Size Exclusion Chromatography Coupled to Mass Spectrometry (MM-SEC-MS)

Separation was performed by an Acquity system (Waters, Milford, MA, USA) coupled to a UV detector and an electrospray mass spectrometer (Thermo Exactive EMR, USA).]. The mass spectrometer was operated in the positive resolution mode and data were recorded from m/z [2000-15,000]. Calibration was achieved on the acquisition range according to manufacturer's procedure.

Example 2. Detection of Fragments in a Digested Mixture of a Bispecific Antibody, Homodimer 1 and Homodimer 2 Using MM-SEC-MS on Zenix-SEC Column 2.1 Sample Preparation of Bispecific Antibody The anti-CD20×anti-CD3 Bispecific Antibody is a hinge-stabilized CD20×CD3 bispecific full-length antibody (Ab) based on an IgG4 isotype modified to reduce Fc binding. It was designed to bind T cells (via CD3) and CD20-expressing cells. The Bispecific Antibody was produced by following the methodology as described by Smith et al. (Sci. Rep. (2015) 5:17943).

2.2 Generation of the Fragments of Bispecific Antibody, Homodimer 1 and Homodimer 2

1 mg of Bispecific antibody was digested with 100 units FabRICATOR® for 60 minutes in 0.1 M Tris-HCl buffer pH 7.5 at 37° C.

2.3 MM-SEC-MS

The analysis using MM-SEC-MS was performed isocratically using a Zenix SEC-300 MK column (4.6×300 nm, 3 μm) on the system as described in Example 1. Elution was monitored by UV at 280 nm.

Eight sets of experiments were carried out wherein the total concentration of the mobile phase was varied: 10 mM buffer, 20 mM buffer, 30 mM buffer, 40 mM buffer, 50 mM buffer, 60 mM buffer, 70 mM buffer, and 75 mM buffer. The elution was carried out at a flow rate of 0.3 mL/min. The chromatography was run on Waters Acquity I-class UPLC system with the column temperature of room temperature. The equilibration was performed using the mobile phase composed of ammonium acetate (buffer A) and ammonium bicarbonate (buffer B) at 14:1 molar ratio.

For analytical runs, the injection loads consisted of 10 μg of the total protein. The elution was carried out using an isocratic gradient consisting of ammonium acetate (buffer A) and ammonium bicarbonate (buffer B). The mass spectrometry data was analyzed by using Intact Mass software.

Figure 4:
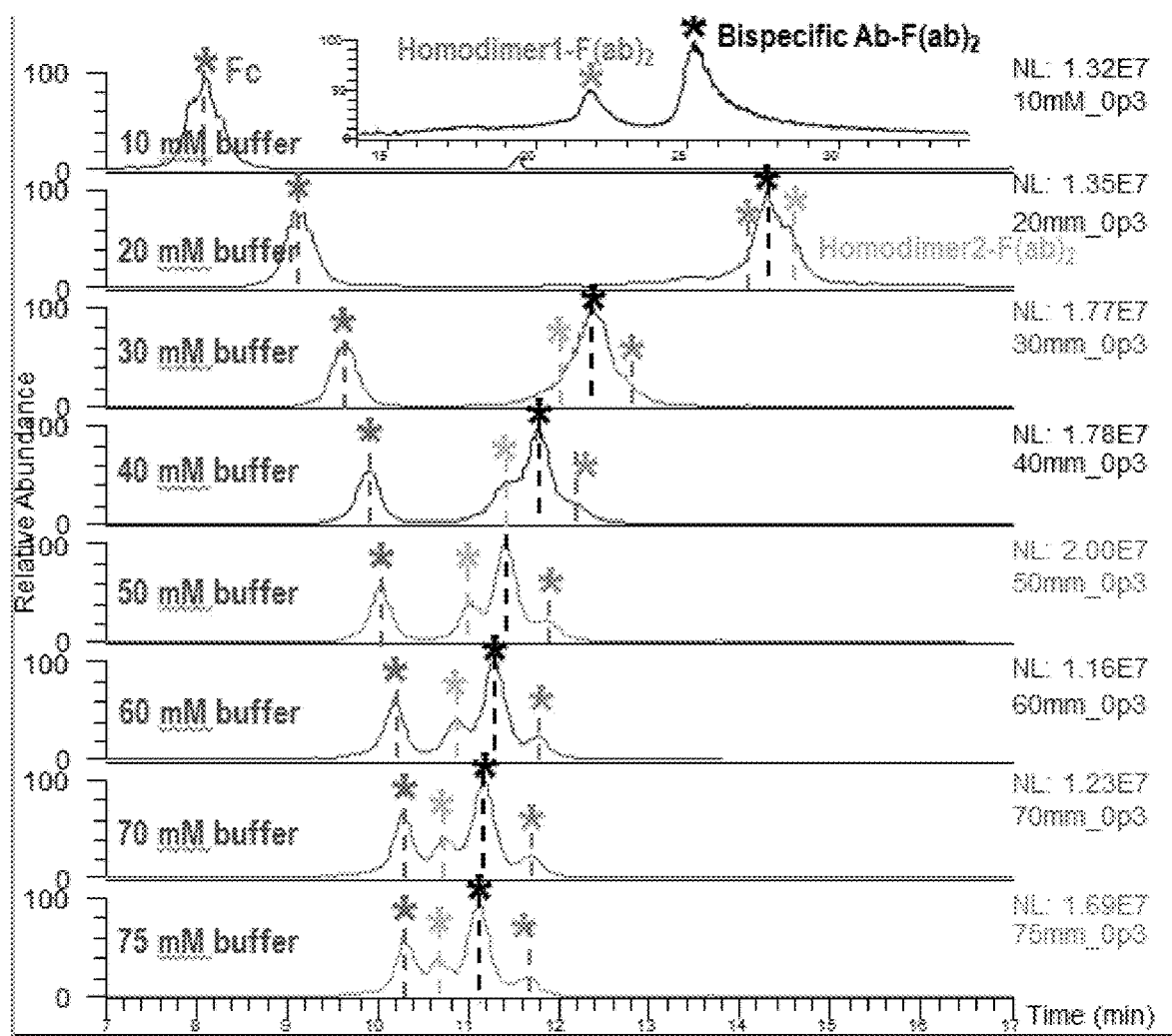
FIG. 4 shows the extracted ion chromatograms (XIC) obtained on performing MM-SEC-MS analysis of a digested mixture of bispecific antibody, homodimer 1, and homodimer 2 using mobile phase with different salt concentration with a flow rate of 0.3 mL/min according to an exemplary embodiment.
Figure 5:
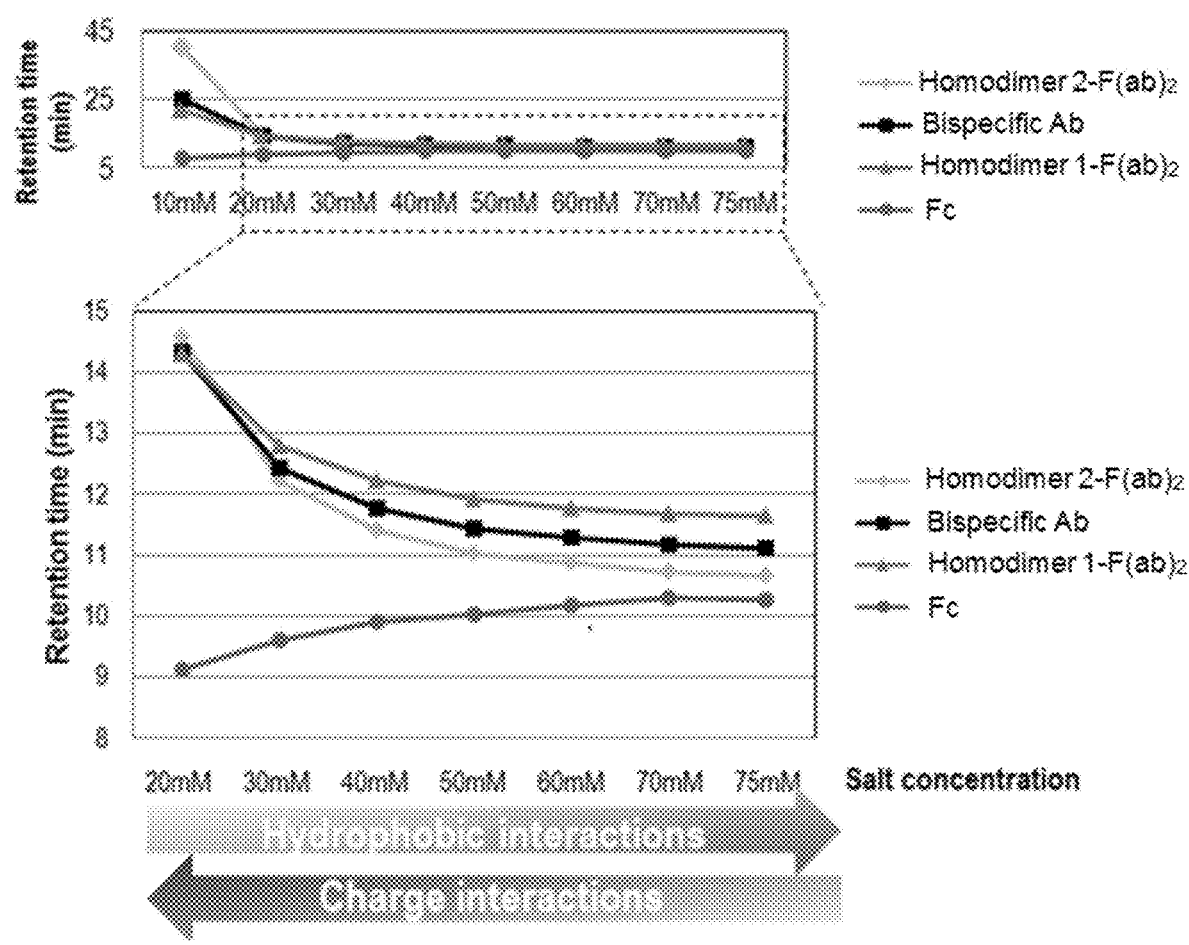
FIG. 5 shows the chart of retention time (minutes) of a protein vs. total salt concentration of the mobile phase for a digested mixture of bispecific antibody, homodimer 1, and homodimer 2 on performing MINI-SEC-MS analysis with a flow rate of 0.3 mL/min according to an exemplary embodiment.

An increased separation between the fragments was observed when lower concentration of mobile phase was used (e.g., for 10 mM buffer concentration, a significant separation between the F(ab)2 fragment of Bispecific Ab, F(ab)2 fragment of Homodimer 1, and Fc fragment was observed (See FIG. 4). Lower salt concentrations enhance the charge-charge interaction in the MM-SEC column, which provided a better separation between the fragments for the Bispecific Ab (See FIGS. 4 and 5).

Example 3. Detection of Fragments in a Digested Mixture of a Bispecific Antibody, Homodimer 1 and Homodimer 2 Using MM-SEC-MS on Zenix-SEC Column 3.1 Sample Preparation of Bispecific Antibody and Generation of the Fragments of Bispecific Antibody, Homodimer 1 and Homodimer was Carried Out as Illustrated in 2.1 and 2.2.

3.2 MM-SEC-MS

The analysis using MM-SEC-MS was performed isocratically using a Zenix SEC-300 MK column (4.6×300 nm, 3 μm) on the system as described in Example 1. Elution was monitored by UV at 280 nm.

Six sets of experiments were carried out wherein the total concentration of the mobile phase was varied: 50 mM buffer, 60 mM buffer, 70 mM buffer, 75 mM buffer, 100 mM buffer, and 300 mM buffer. The elution was carried out at a flow rate of 0.2 mL/min. The chromatography was run on Waters Acquity I-class UPLC system with the column temperature of room temperature. The equilibration was performed using the mobile phase.

For analytical runs, the injection loads consisted of 10 μg of the total protein. The elution was carried out using an isocratic gradient consisting of ammonium acetate (buffer A) and ammonium bicarbonate (buffer B). The mass spectrometry data was analyzed by using Intact Mass software from Protein Metrics.

Figure 6:
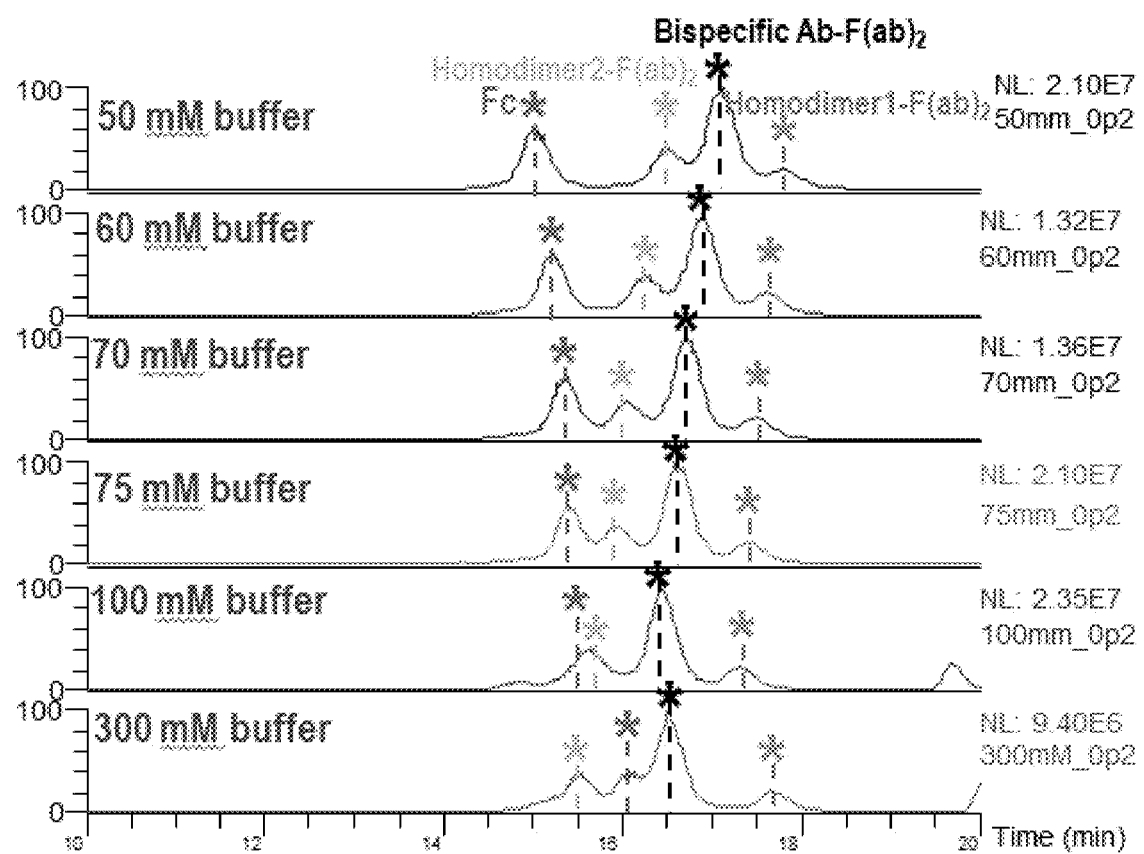
FIG. 6 shows the extracted ion chromatograms (XIC) obtained on performing MM-SEC-MS analysis of digested mixture of bispecific antibody, homodimer 1, and homodimer 2 using mobile phase with different salt concentration with a flow rate of 0.2 mL/min according to an exemplary embodiment.
Figure 7:
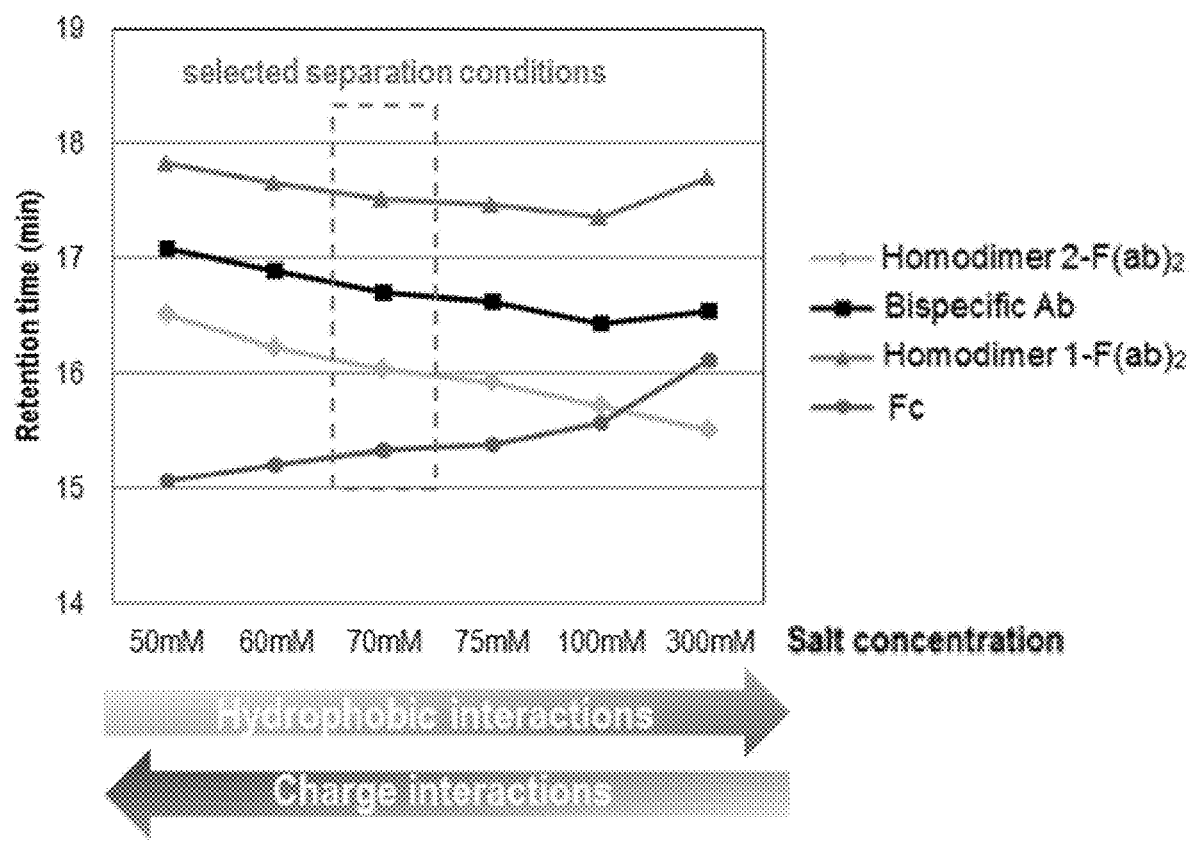
FIG. 7 shows the chart of retention time (minutes) of a protein vs. total salt concentration of the mobile phase for a digested mixture of bispecific antibody, homodimer 1, and homodimer 2 on performing MINI-SEC-MS analysis with a flow rate of 0.2 mL/min according to an exemplary embodiment.
Figure 8:
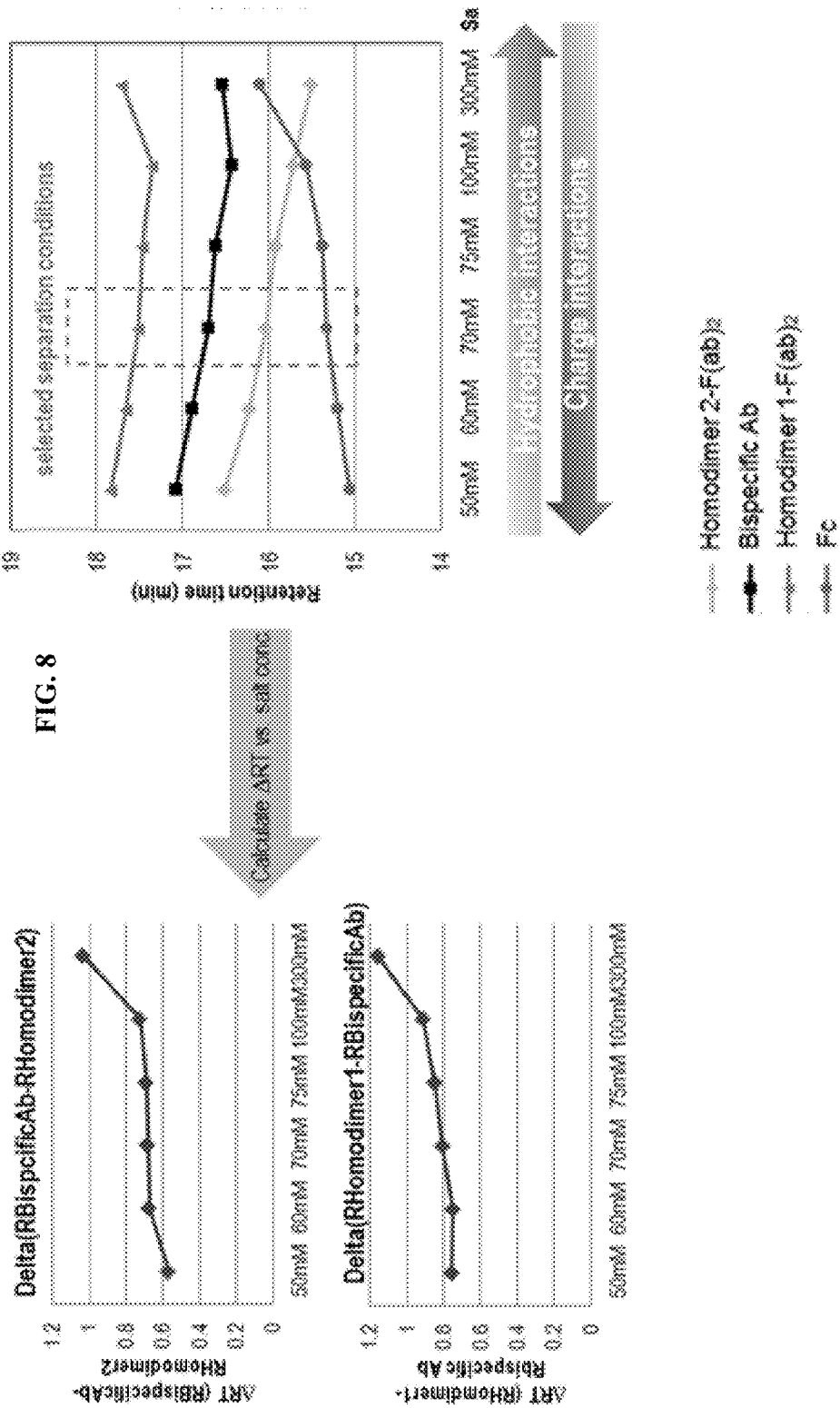
FIG. 8 shows the effect of concentration of mobile phase on the separation of digested mixture of F(ab)2 fragments of bispecific antibody, homodimer 1, and homodimer 2 on performing MM-SEC-MS analysis according to an exemplary embodiment.

Lower salt concentrations enhance the charge-charge interaction in the MM-SEC column and higher salt concentrations enhance the hydrophobic interaction in the MM-SEC column. At 50 mM buffer concentration, the system showed a better separation between the F(ab)2 fragment of the bispecific antibody and the Fc fragment, whereas at 300 mM, the system showed a better separation between the F(ab)2 fragment of the bispecific antibody and the F(ab)2 fragment of the homodimer 1 (See FIGS. 6 and 7). The difference in retention times of the F(ab)2 fragments for bispecific antibody and homodimer 1 and of the F(ab)2 fragments for bispecific antibody and homodimer 2 further shows that a better separation was attained at high buffer concentration of 300 mM (FIG. 8).

Example 4. Detection of Fragments of an Antibody Molecule (Ab1) Using Zenix SEC-300, 3 µm, 300 Å, 7.8×300 mm 4.1 Generation of the Fragments of Ab1

0.5 mg of Ab1 was digested with [50 unit] FabRICATOR® for 60 minutes in 0.1 M Tris-HCl buffer pH 7.5 at 37° C. to form fragments.

4.2 MM-SEC-MS

The analysis using MM-SEC-MS was performed isocratically using a Zenix SEC-300 MK column (4.6×300 nm, 3 µm) on the system as described in Example 1. Elution was monitored by UV at 280 nm.

Five sets of experiments were carried out wherein the total concentration of the mobile phase was varied: 30 mM buffer, 40 mM buffer, 66 mM buffer, 100 mM buffer, and 200 mM buffer. The elution was carried out at a flow rate of 0.2 mL/min. The chromatography was run on Waters Acquity I-Class UPLC system with the column temperature of room temperature. The equilibration was performed using the mobile phase.

For analytical runs, the injection loads consisted of 10 µg of the total protein. The elution was carried out using an isocratic gradient consisting of ammonium acetate (buffer A) and ammonium bicarbonate (buffer B). The mass spectrometry data was analyzed by using Intact Mass software from Protein Metrics.

Figure 9:
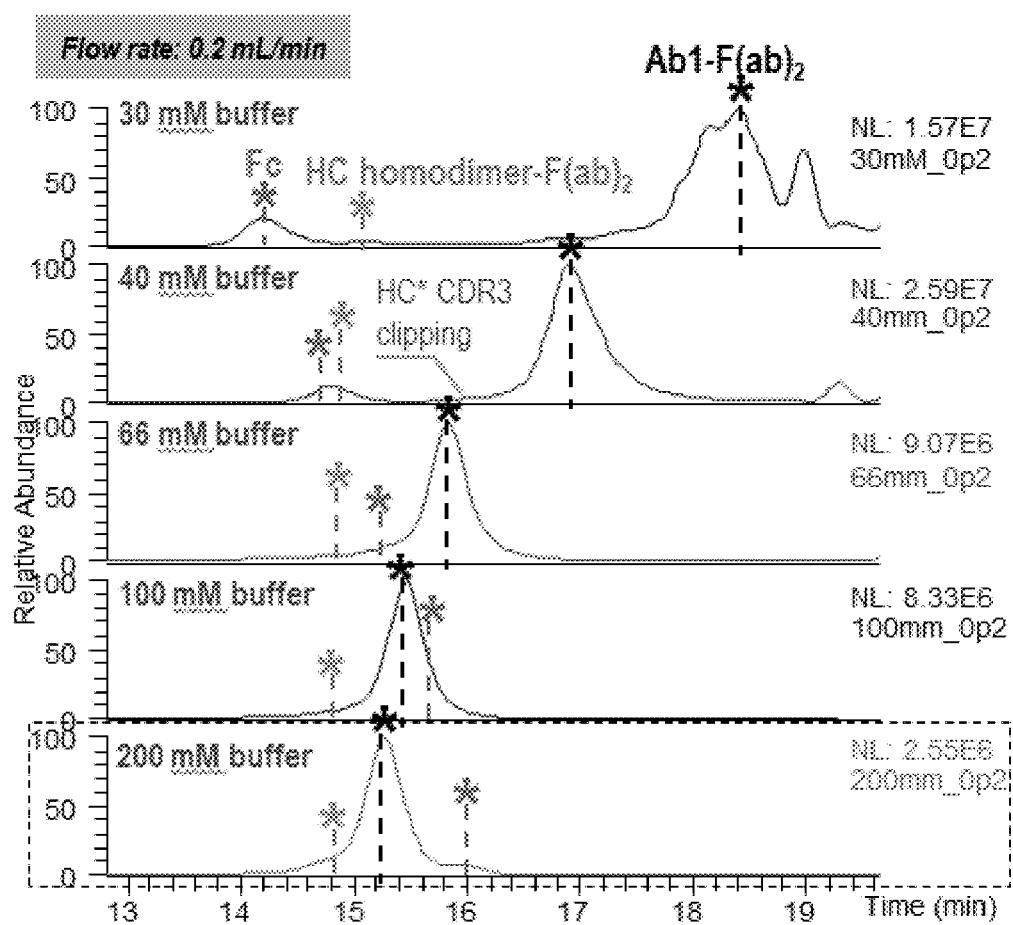
FIG. 9 shows the extracted ion chromatograms (XIC) obtained on performing MM-SEC-MS analysis of digested and deglycosylated mixture of an antibody using mobile phase with different salt concentration with a flow rate of 0.2 mL/min according to an exemplary embodiment.
Figure 10:
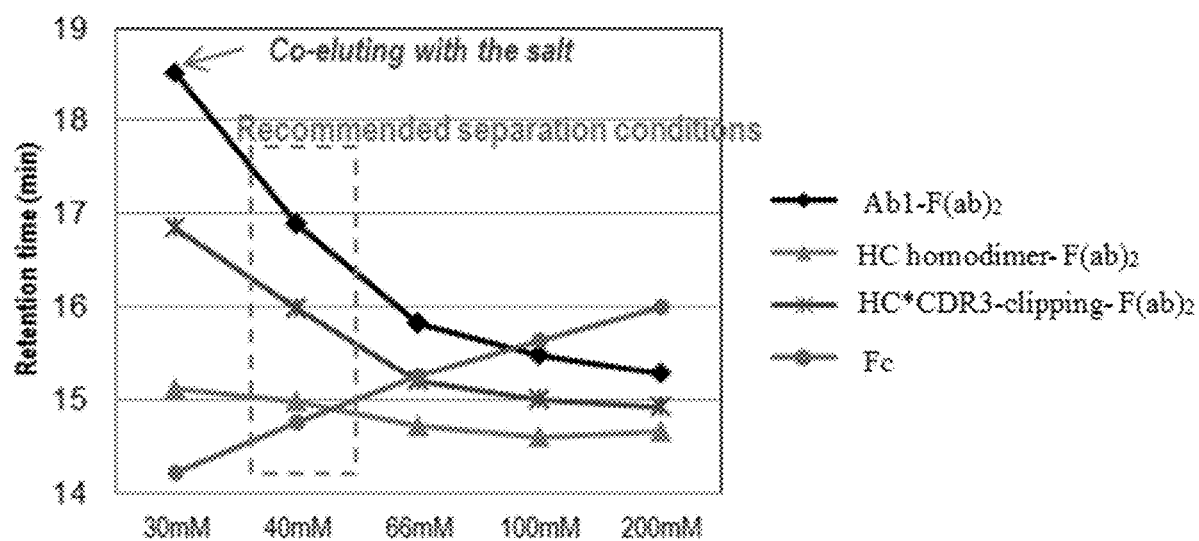
FIG. 10 shows the chart of retention time (minutes) of a protein vs. total salt concentration of the mobile phase for a digested and deglycosylated mixture of an antibody on performing MINI-SEC-MS analysis with a flow rate of 0.2 mL/min according to an exemplary embodiment.
Figure 11:
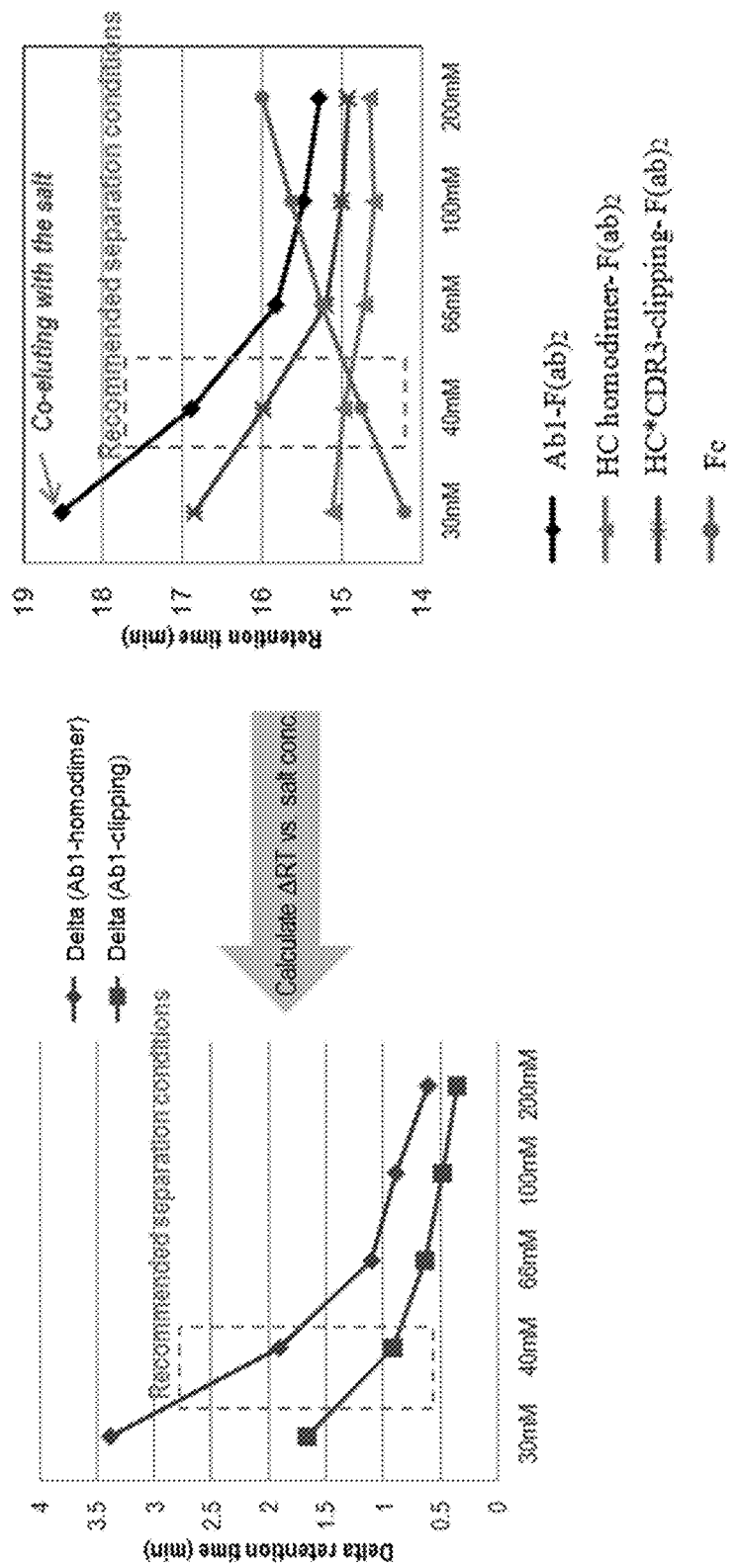
FIG. 11 shows the effect of concentration of mobile phase on the separation of digested and deglycosylated mixture of an antibody on performing MINI-SEC-MS analysis with a flow rate of 0.2 mL/min according to an exemplary embodiment.

The runs with mobile phases of differing concentration revealed that lower salt concentration enhancing the charge-charge interaction in the MM-SEC column providing better separation of the fragments (See FIGS. 9 and 10). Comparing the retention times of Fc fragment of Ab1 and F(ab)2 fragment of Ab1, the mobile phase concentration of 30 mM provides the best separation. Further, the difference in retention time of the HC homodimer-F(ab)2 and HC*CDR3 clipping product further shows that a better separation was attained at the low buffer concentration of 30 mM (FIG. 11).

Figure 12:
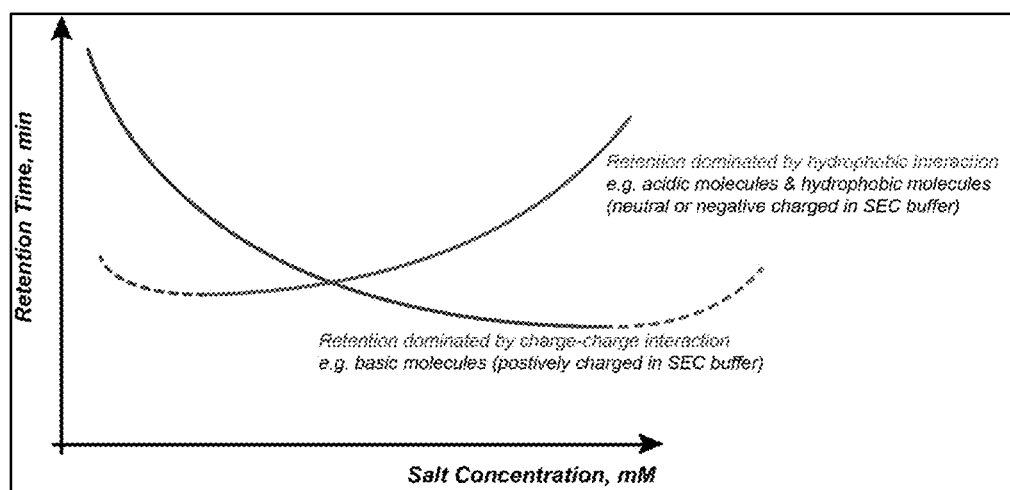
FIG. 12 represents a chart showing a trend in retention time on changing total salt concentration when performing MM-SEC-MS analysis according to an exemplary embodiment.
Figure 13:
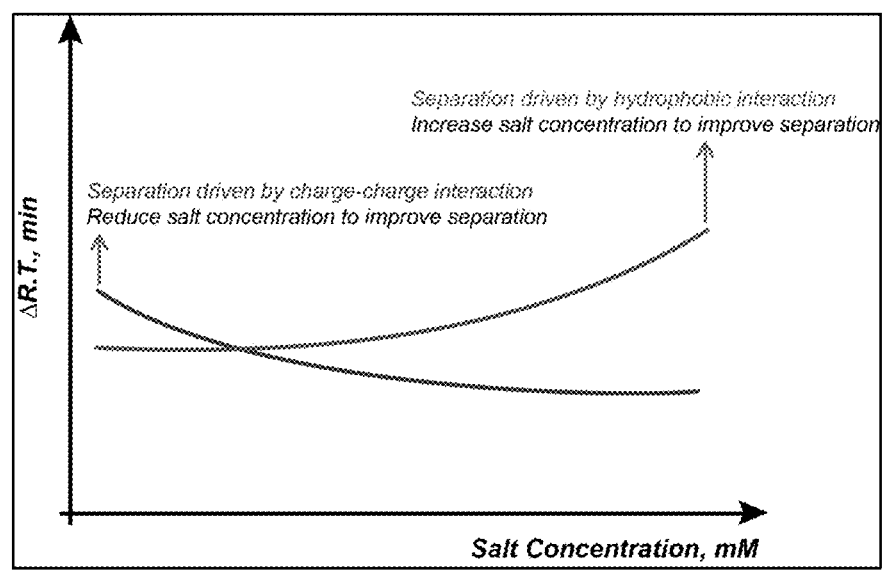
FIG. 13 represents a chart showing a trend in difference in retention time on changing total salt concentration when performing MINI-SEC-MS analysis according to an exemplary embodiment.

The fragments as illustrated in examples 1-3 show better separation at different buffer concentrations. This effect could be due to different types of interaction: charge, shape, or hydrophobicity of the proteins with the size exclusion chromatography resin used. The charge on the protein at a given salt concentration depends on pI values (Tables 1 and 2). Significant differences in charge interactions with the MM-SEC media are obtained with larger differences in pI values. For the same class of IgG molecules, differences in hydrophobicity originate from the Fab region. At lower salt concentrations, retention time can be driven by charge-charge interaction and at higher salt concentrations, retention is driven by hydrophobic interaction. Thus, acidic or hydrophobic molecules can be separated by using mobile phase with higher salt concentration in the MM-SEC-MS system and basic molecules can be separated by using mobile phase with lower salt concentration in the MM-SEC-MS system (See FIG. 12 and FIG. 13).

TABLE 1

| mAb isotype | molecule | intact | | F(ab)2 | | Fc |
| --- | --- | --- | --- | --- | --- | --- |
| | | pI | MW | pI | MW | pI |
| IgG4 | Bispecific Ab | 7.66 | 145,337 | 8.32 | 97,827 | 5.81 |
| | homodimer 1 | 7.28 | 144,677 | 8.13 | 98,491 | 5.77 |
| | homodimer 2 | 8.03 | 145,998 | 8.48 | 97,164 | 5.86 |

TABLE 2

| mAb isotype | molecule | intact | | F(ab)2 | | Fc |
| --- | --- | --- | --- | --- | --- | --- |
| | | pI | MW | pI | MW | pI |
| IgG4 | Ab1 | 7.59 | 145,544 | 8.29 | 98,052 | 5.81 |
| | Ab1 HC/HC homodimer | 6.57 | 145,948 | 6.98 | 98,445 | 5.77 |

Example 5. Detection of Fragments in a Digested Mixture of a Bispecific Antibody, Homodimer 1 and Homodimer 2 Using MM-SEC-MS on Waters BEH SEC Column 5.1 Sample Preparation of Bispecific Antibody and Generation of the Fragments of Bispecific Antibody, Homodimer 1 and Homodimer was Carried Out as Illustrated in 2.1 and 2.2.

5.2 MM-SEC-MS

The analysis using MM-SEC-MS was performed isocratically using a Waters BEH SEC column (4.6×300 nm, 3 µm) on the system as described in Example 1. Elution was monitored by UV at 280 nm.

Eight sets of experiments were carried out wherein the total concentration of the mobile phase was varied: 20 mM buffer, 27.6 mM buffer, 30 mM buffer, 40 mM buffer, 50 mM buffer, 100 mM buffer, 150 mM buffer, and 300 mM buffer. The elution was carried out at a flow rate of 0.2 mL/min. The chromatography was run on Waters Acquity I-class UPLC system with the column temperature of room temperature. The equilibration was performed using the mobile phase.

For analytical runs, the injection loads consisted of 10 µg of the total protein. The elution was carried out using an isocratic gradient consisting of ammonium acetate (buffer A) and ammonium bicarbonate (buffer B). The mass spectrometry data was analyzed by using Intact Mass software.

Figure 14:
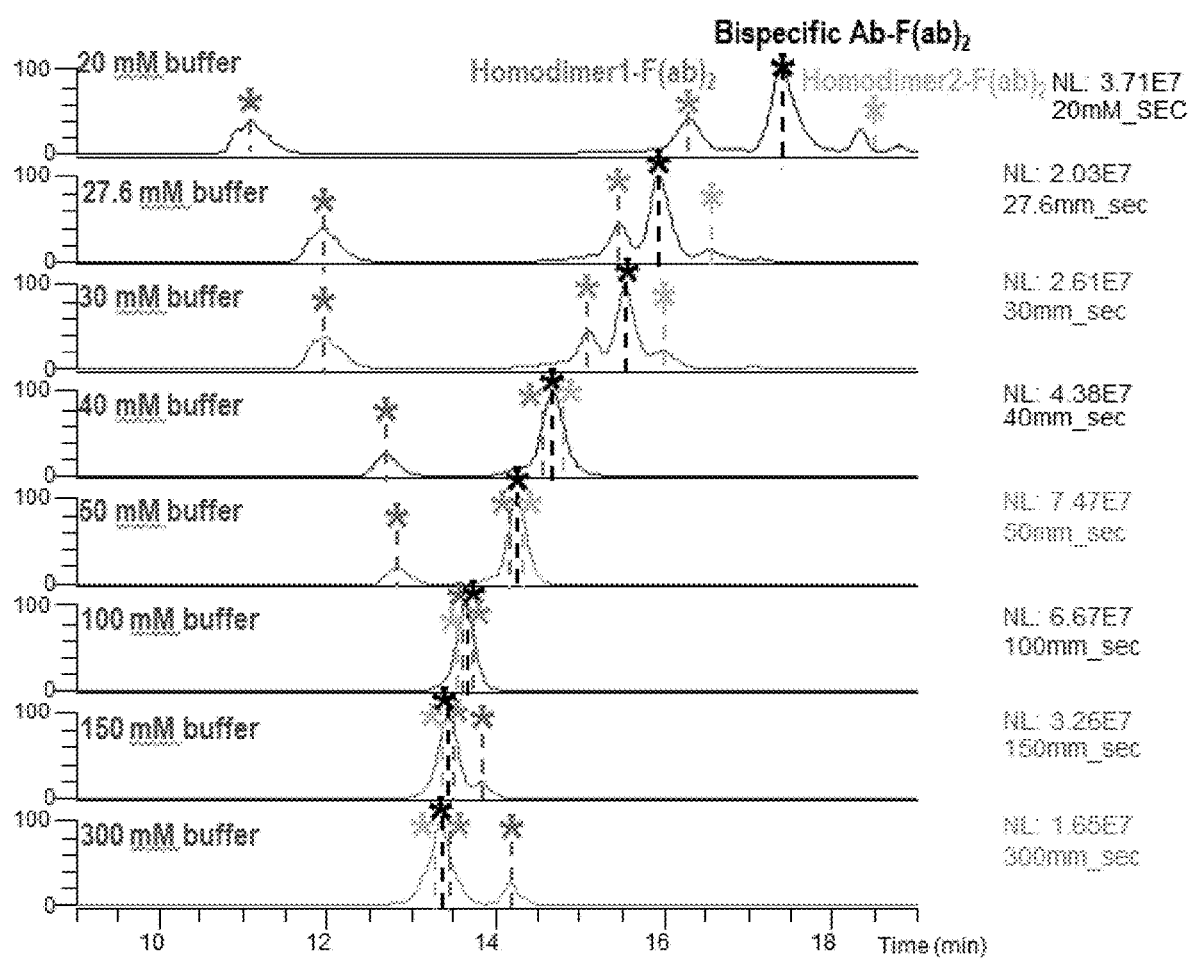
FIG. 14 shows the extracted ion chromatograms (XIC) obtained on conducting MM-SEC-MS analysis of digested mixture of bispecific antibody, homodimer 1, and homodimer 2 when performing MM-SEC-MS on Waters BEH SEC Column according to an exemplary embodiment.
Figure 15:
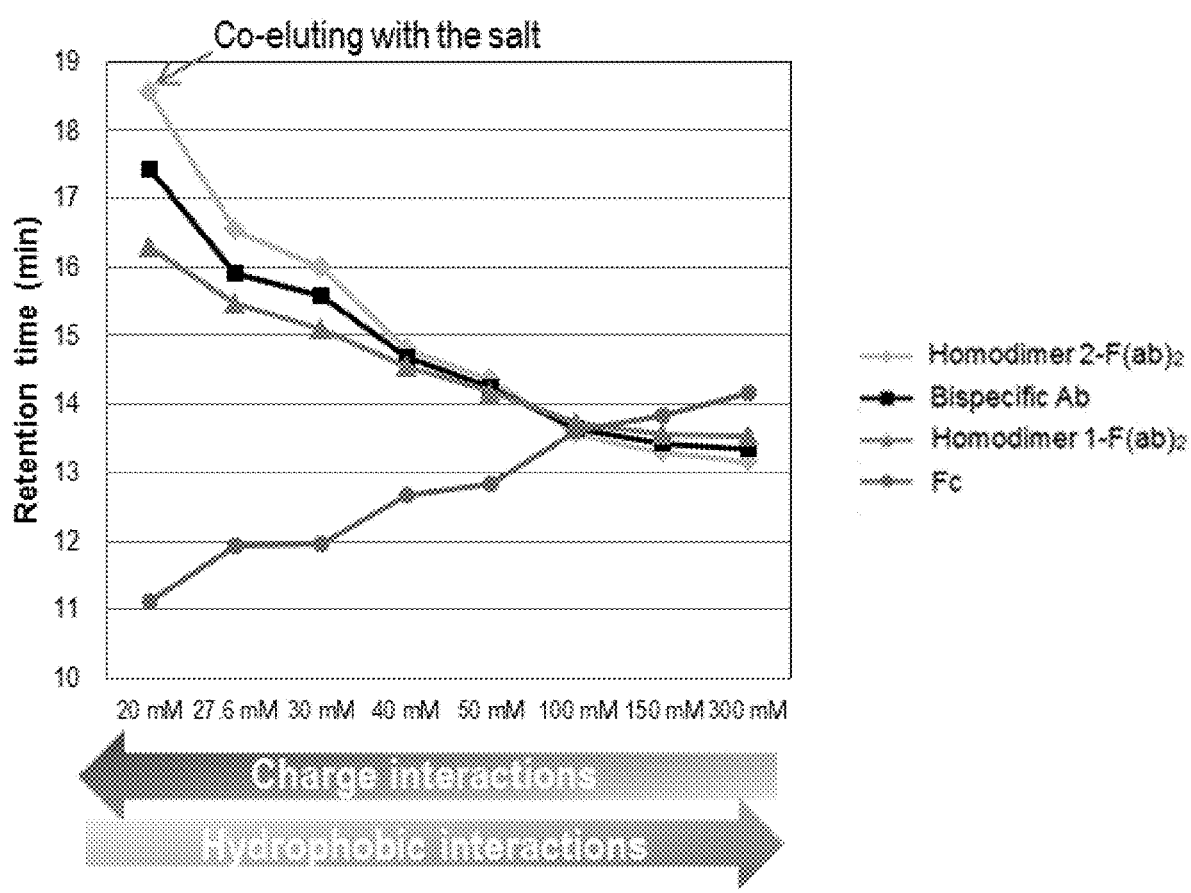
FIG. 15 shows the chart of retention time (minutes) of a protein vs. total salt concentration of the mobile phase for a digested mixture of bispecific antibody, homodimer 1, and homodimer 2 when performing MM-SEC-MS analysis on Waters BEH SEC Column according to an exemplary embodiment.

Similar to the process carried on a Zenix SEC column, MM-SEC-MS analysis of digested mixture of bispecific Ab, homodimer 1, and homodimer 2 exhibited larger separations at lower concentration of buffer, i.e., 20 mM buffer (See FIGS. 14 and 15).

Example 6. Identification of a New HC*CDR3 Clipping Site in Ab1 Using MM-SEC-MS 6.1 Generation of the Fragments of Ab1

The fragments of Ab1 were generated using the methodology as describe in 4.1

6.2 MM-SEC-MS

The analysis using MM-SEC-MS was performed isocratically using a Zenix SEC column (4.6×300 nm, 3 µm) on the system as described in Example 1. Elution was monitored by UV at 280 nm.

The analysis was carried out using a mobile phase with total concentration of 40 mM buffer and the elution was carried out at a flow rate of 0.2 mL/min. The chromatography was run on Waters Acquity I-class UPLC system with the column temperature of room temperature. The equilibration was performed using the mobile phase.

Figure 16:
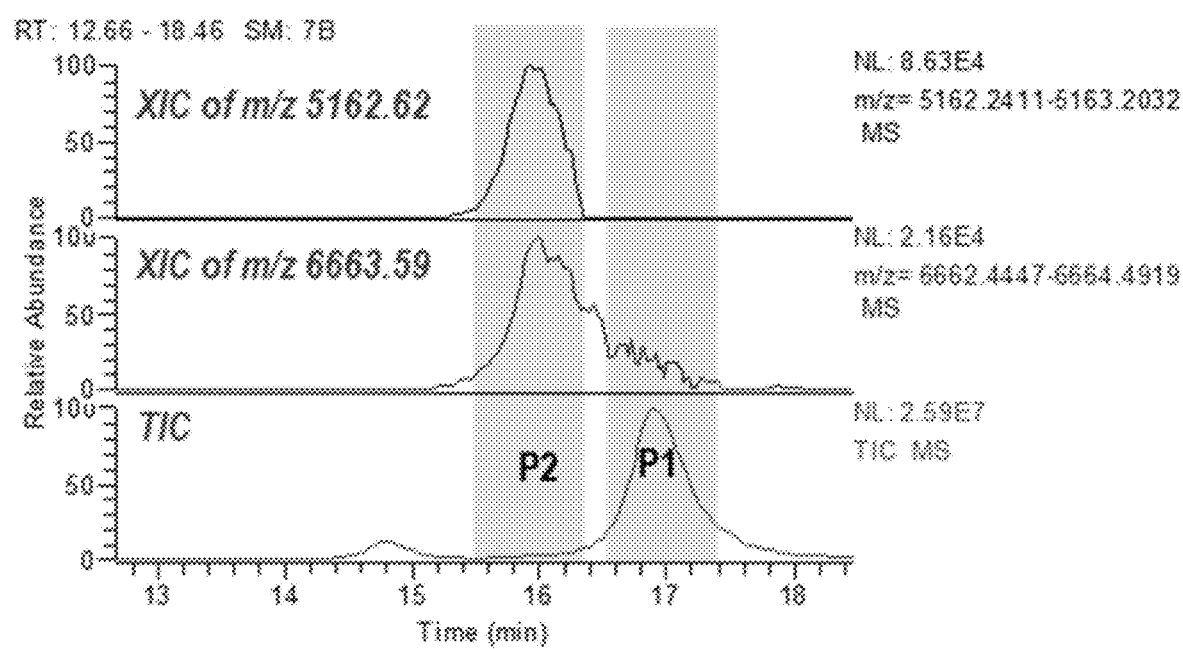
FIG. 16 shows the relative abundance of a protein vs. retention time (minutes) for a digested and deglycosylated mixture of an antibody on performing MM-SEC-MS analysis using 40 mM SEC buffer according to an exemplary embodiment.
Figure 17:
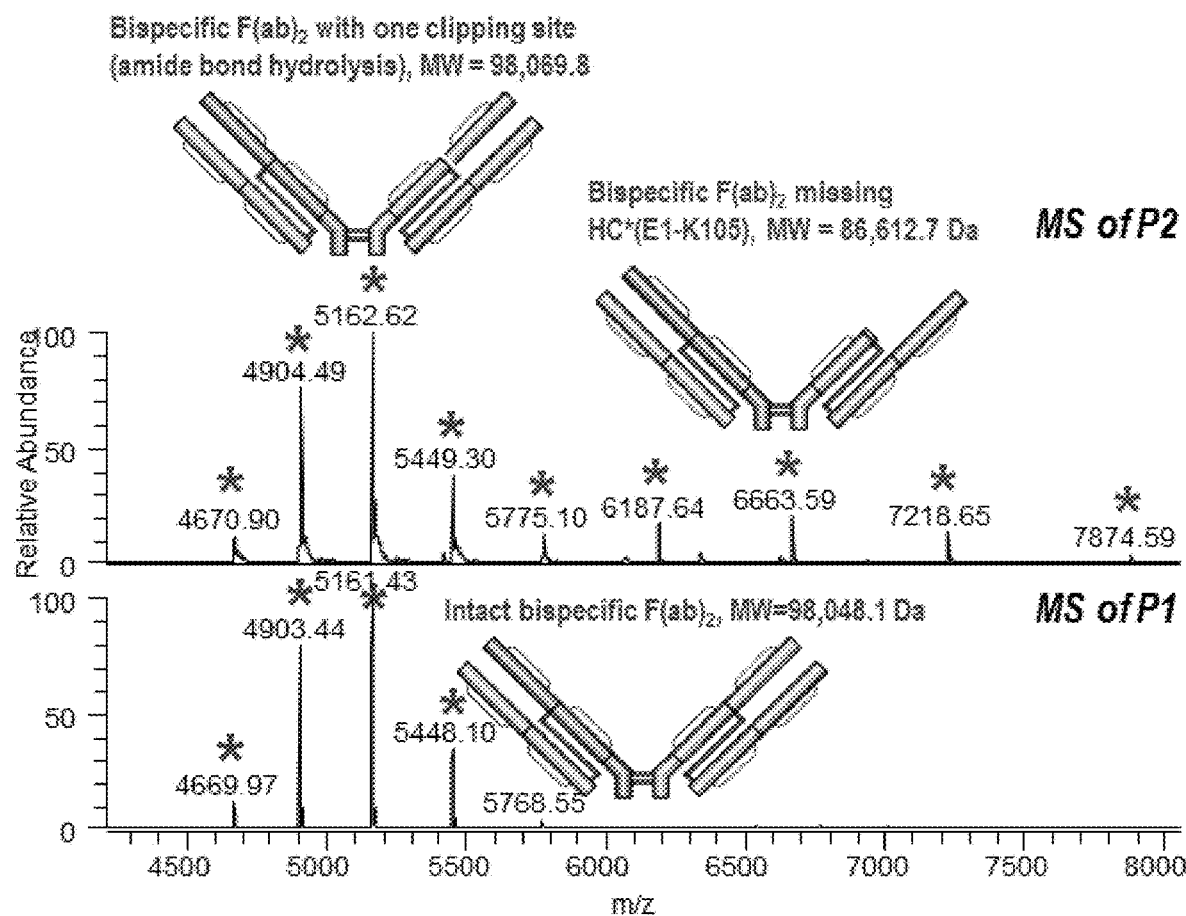
FIG. 17 shows the chart of retention abundance of a protein vs. mass to charge ratio of the protein for a digested and deglycosylated mixture of an antibody on performing MM-SEC-MS analysis according to an exemplary embodiment.

For analytical runs, the injection loads consisted of 10 μg of the total protein. The elution was carried out using an isocratic gradient consisting of ammonium acetate (buffer A) and ammonium bicarbonate (buffer B). The mass spectrometry data was analyzed by using Intact Mass software from Protein Metrics. The total ion chromatogram for the sample showed two peaks with retention times of 16 minutes and 17 minutes. The mass analysis of one of the peaks had fragments with mass to charge ratio of 5162.62 and 6663.59 (See FIG. 16). This peak at 16 min showed two m/z peak distributions, one with one of the charge state being 5162.62 corresponds to the amide bond hydrolysis between K105 and F106 but the fragments are still held together by non-covalent interactions, the other m/z peak distributions (one of the charge state being m/z 6663.59) correspond to the dissociated fragment from the hydrolysis product. The other peak showed a fragment with mass to charge ratio of 5161.43 (FIGS. 16 and 17). The masses were compared to the calculations based on the Ab1 sequence and identified to be the Bispecific Ab-F(ab)2 with one clipping site (amide bond hydrolysis) (MW=98,069.8), Bispecific Ab-F(ab)2 missing HC*(E1-K105) (MW=86,612.7), and intact Bispecific Ab F(ab)2 (MW=98,048.1). These fragments led to identification the site if fragmentation in the HC of the Bispecific Ab: between Lysine105 and Phenylalanine106.

6.3 Confirmation of the HC*CDR3 Clipping Site by Native SCX-MS

The analysis using strong cation chromatography was performed using a YMC BioPro SP-F column (4.6×100 nm). Elution was monitored by UV at 280 nm. Separation was performed by an Acquity system (Waters, Milford, MA, USA) coupled to a UV detector and an electrospray mass spectrometer (Thermo Exactive EMR, USA). The mass spectrometer was operated in the positive resolution mode and data were recorded from m/z 2000-15,000. Calibration was achieved on the acquisition range according to manufacturer's procedure.

The analysis was carried out using gradient elution at a flow rate of 4 mL/min: 100% A to 100% B in 18 min; wherein solvent A was 20 mM ammonium acetate, pH 5.6 and solvent B was 140 mM ammonium acetate+10 mM ammonium bicarbonate. The equilibration was performed using the mobile phase.

Figure 18:
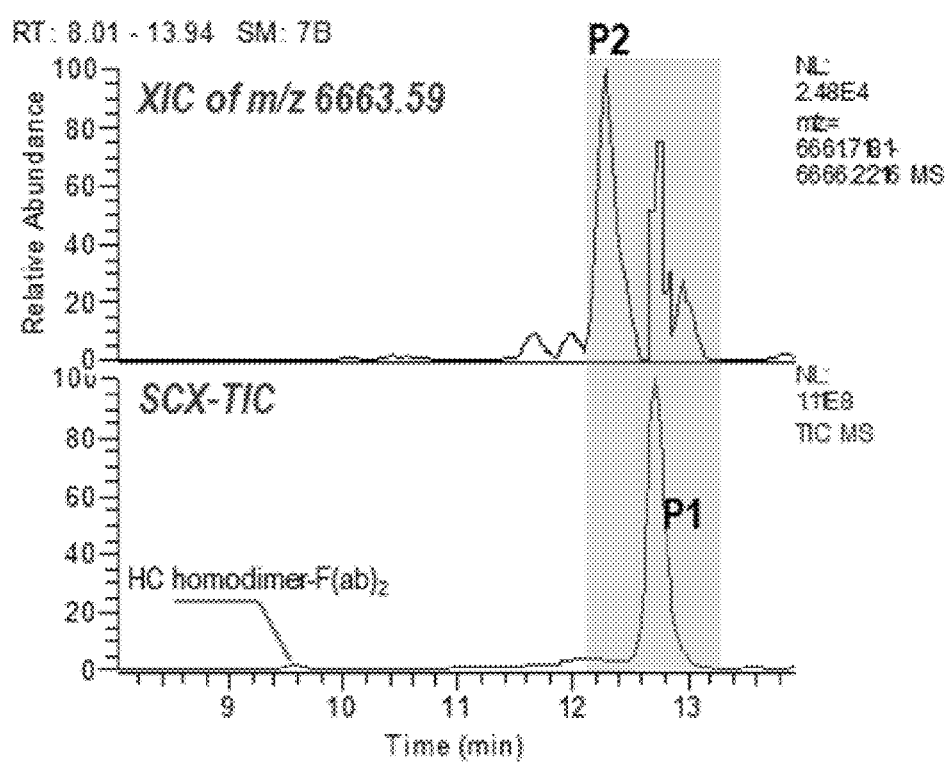
FIG. 18 shows the relative abundance of a protein vs. retention time (minutes) for a digested and deglycosylated mixture of an antibody on performing MM-SEC-MS analysis using a native strong-cation-exchange chromatography-mass spectrometry.
Figure 19:
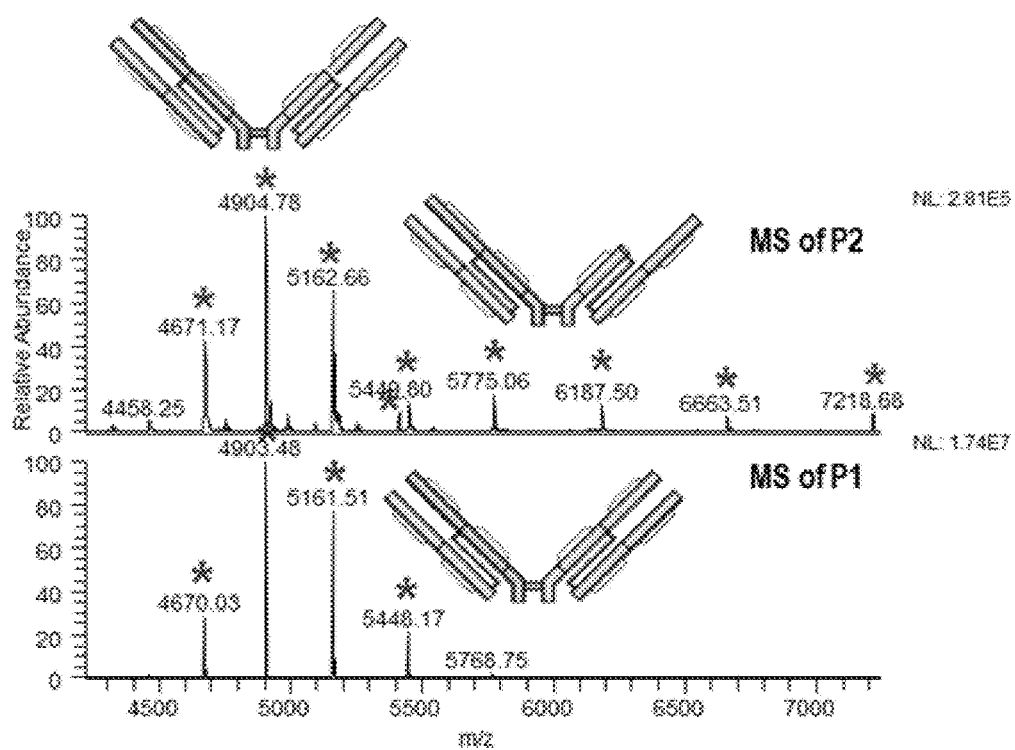
FIG. 19 shows the chart of retention abundance of a protein vs. mass to charge ratio of the protein for a digested and deglycosylated mixture of an antibody analysis using a native strong-cation-exchange chromatography-mass spectrometry.

For analytical runs, the injection loads consisted of 50 μg of the total protein. The elution was carried as describe above. The mass spectrometry data was analyzed by using Intact Mass software from Protein Metrics. The chromatogram for the sample showed two peaks with retention times of 12 minutes and 13 minutes. The mass analysis of one of the peaks had fragments with mass to charge ratio of 5162.66 and 6663.51. The other peak showed a fragment with mass to charge ratio of 5161.51 (FIGS. 18 and 19), which confirmed the fragments obtained by using the MM-SEC-MS system: Bispecific Ab-F(ab)2 with one clipping site (amide bond hydrolysis) (MW=98,069.8), Bispecific Ab-F(ab)2 missing HC*(E1-K105) (MW=86,612.7), and intact Bispecific Ab F(ab)2 (MW=98,048.1).

Figure 20:
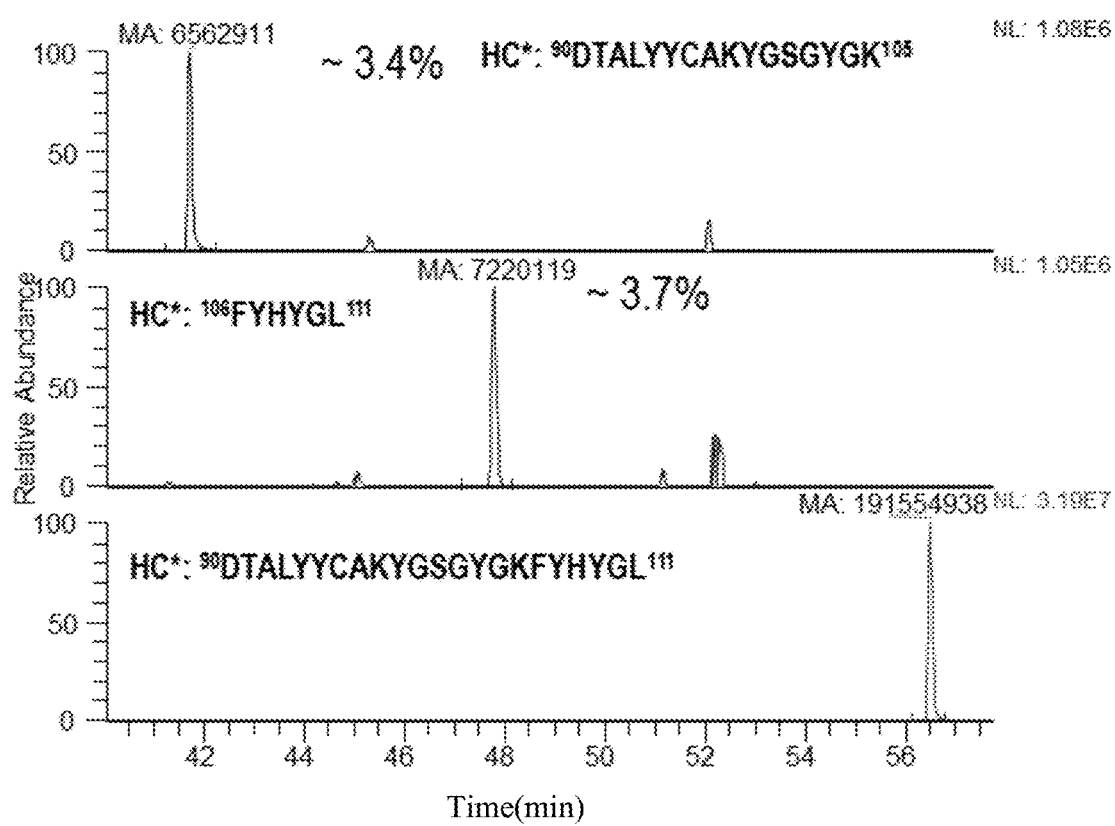
FIG. 20 shows quantification of fragments obtained from Asp-N protease digestion of an antibody according to an exemplary embodiment.

6.4 Quantitation of the HC*CDR3 Clipping Fragment 100 ug of HC*CDR3 clipping fragment was digested with 2 ug AspN enzyme for 18 hours in 0.1 M Tris-HCl buffer pH 7.5 at 37° C. to form its fragments. The chromatography of the fragment using PepMap column provided a quantification of the HC*CDR3 clipping fragment of Ab1 (FIG. 20).

6.5 Susceptibility of Ab1 to Plasma Proteases to Form HC*CDR3 Clipping Fragment in Vivo MM-SEC-MS analysis of digested fragments formed by was performed isocratically using a Zenix SEC-300 MK column (4.6×300 nm, 3 μm) on the system as described in Example 1. Elution was monitored by UV at 280 nm. Trypsin enzyme was used to predict the susceptibility of Ab1 in vivo to plasma proteases to form the HC*CDR3 Clipping fragment (identified in example 6.2). To the digested fragments of Ab1 antibody as described in 4.1, trypsin was added in the ratio of 200:1 at 37° C.

An injection load consisting of 10 μg of the total protein was loaded on the column. The analysis was performed using a mobile phase with total concentration of 30 mM (ammonium acetate (buffer A) and ammonium bicarbonate) and the elution was carried out at a flow rate of 0.2 mL/min. The chromatography was run on Waters Acquity I-Class UPLC system with the column temperature of room temperature.

Figure 21:
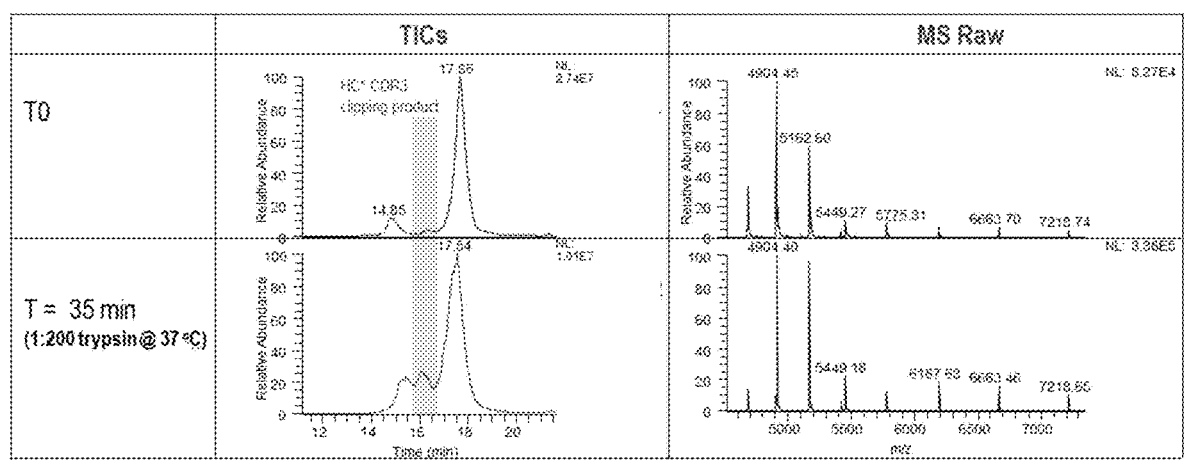
FIG. 21 shows the susceptibility of an antibody to fragment in vivo by using identification and quantification of fragments obtained from trypsin protease digestion of the antibody according to an exemplary embodiment.

At time zero of addition of the trypsin enzyme, the fragmentation showed a presence of HC*CDR3 Clipping fragment (FIG. 21, upper panel). On similar analysis at time equal to 35 minutes after addition of the trypsin enzyme, the fragmentation showed a significant increase in presence of HC*CDR3 clipping fragment (FIG. 21, lower panel). This indicated that the antibody Ab1 is cleaved at the site (K105-F106) by trypsin, suggesting that the antibody Ab1 in vivo is susceptible to such a cleavage in vivo.

What is claimed is:

1. A method for quantification of a fragment of an antibody in a sample, said method comprising:
   contacting the sample to a chromatographic system having a mixed-mode size-exclusion chromatography resin with a charge-charge interaction functionality;
   washing the mixed-mode size-exclusion chromatography resin using a mobile phase to provide an eluent with the fragment; and
   quantifying the amount of the fragment of the antibody.

2. The method of claim 1, wherein the mobile phase can be selected from ammonium acetate, ammonium bicarbonate, or ammonium formate, or combinations thereof.

3. The method of claim 1, wherein the fragment is a degradation product of the antibody.

4. The method of claim 1, wherein the antibody is a monoclonal antibody.

5. The method of claim 1, wherein the antibody is a therapeutic antibody.

6. The method of claim 1, wherein the antibody is a bispecific antibody.

7. The method of claim 1, wherein the fragment can be a digestion product of the antibody.

8. The method of claim 1, wherein the mass spectrometer can be a tandem mass spectrometer.

9. A method for identifying a fragment of an antibody in a sample, said method comprising;
   contacting the sample to a chromatographic system having a mixed-mode size-exclusion chromatography resin with a charge-charge interaction functionality;
   washing the mixed-mode size-exclusion chromatography resin using a mobile phase to provide an eluent with the fragment;
   determining the molecular weight of the fragment in the eluent using a mass spectrometer, wherein the mass spectrometer is coupled to the chromatographic system; and correlating the molecular weight data of the fragment to data obtained from at least one known protein standard to identify said fragment of said antibody;

wherein the fragment is a degradation product of the antibody or the fragment is a digestion product of the antibody.

10. The method of claim 9, wherein the mobile phase can be selected from ammonium acetate, ammonium bicarbonate, or ammonium formate, or combinations thereof.

11. The method of claim 9, wherein the antibody is a monoclonal antibody.

12. The method of claim 9, wherein the antibody is a therapeutic antibody.

13. The method of claim 9, wherein the antibody is a bispecific antibody.

14. The method of claim 9, wherein the mass spectrometer can be a tandem mass spectrometer.

15. A method for identifying a fragment of an antibody in a sample, said method comprising;

contacting the sample to a chromatographic system having a mixed-mode size-exclusion chromatography resin with a charge-charge interaction functionality;

washing the mixed-mode size-exclusion chromatography resin using a mobile phase to provide an eluent with the fragment;

determining the molecular weight of the fragment in the eluent using a mass spectrometer, wherein the mass spectrometer is coupled to the chromatographic system; and correlating the molecular weight data of the fragment to data obtained from at least one known protein standard to identify said fragment of said antibody;

wherein the mass spectrometer is a tandem mass spectrometer.

16. The method of claim 15, wherein the mobile phase can be selected from ammonium acetate, ammonium bicarbonate, or ammonium formate, or combinations thereof.

17. The method of claim 15, wherein the antibody is a monoclonal antibody.

18. The method of claim 15, wherein the antibody is a therapeutic antibody.

19. The method of claim 15, wherein the antibody is a bispecific antibody.

20. The method of claim 15, wherein the fragment is a degradation product of the antibody.

21. The method of claim 15, wherein the fragment is a digestion product of the antibody.

* * * * *